(12) United States Patent
DeHennis et al.

(10) Patent No.: US 10,872,048 B2
(45) Date of Patent: Dec. 22, 2020

(54) REMOTELY-POWERED SENSING SYSTEM WITH MULTIPLE SENSING DEVICES

(71) Applicant: Senseonics Incorporated, Germantown, MD (US)

(72) Inventors: Andrew DeHennis, Germantown, MD (US); Abhi Chavan, Germantown, MD (US); James Masciotti, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 392 days.

(21) Appl. No.: 15/709,679

(22) Filed: Sep. 20, 2017

(65) Prior Publication Data

US 2018/0137070 A1 May 17, 2018

Related U.S. Application Data

(63) Continuation-in-part of application No. 15/482,141, filed on Apr. 7, 2017, now Pat. No. 10,102,178, (Continued)

(51) Int. Cl.
*G06F 13/28* (2006.01)
*H04B 5/00* (2006.01)
(Continued)

(52) U.S. Cl.
CPC .......... *G06F 13/287* (2013.01); *G01N 33/50* (2013.01); *H02J 50/10* (2016.02); *H04B 5/0037* (2013.01); *H04B 5/0075* (2013.01); *Y02D 10/00* (2018.01)

(58) Field of Classification Search
CPC .... G06F 13/287; G01N 33/50; H04B 5/0037; H04B 5/0075; H02J 50/10; Y02D 10/14
See application file for complete search history.

(56) References Cited

U.S. PATENT DOCUMENTS 4,203,096 A 5/1980 Farley et al.
6,561,978 B1 5/2003 Conn et al.
(Continued)

OTHER PUBLICATIONS

Colvin et al "Increased in vivo stability and functional lifetime of an implantable glucose sensor through platinum catalysis", Journal of Biomedical Materials Research Part A, vol. 101A, Issue 5, pp. 1274-1282, Oct. 15, 2012.

*Primary Examiner* — Dennis White
(74) *Attorney, Agent, or Firm* — Rothwell, Figg, Ernst & Manbeck, P.C.

(57) ABSTRACT

A sensing system including analyte sensing devices, an interface device, and shared communication device. The interface device may be configured to receive a power signal and generate power for powering the sensing devices and to convey data signals generated by the sensing devices. The sensing system may be configured to receive addressed and unaddressed commands. The sensing devices may be configured to perform activities (e.g., measurement sequences) in parallel in response to the unaddressed commands (e.g., unaddressed measurement commands). The sensing devices may be configured to only perform activities (e.g., conveying measurement data) in response to addressed commands (e.g., addressed read measurement data commands) if the sensing devices determine that the addressed commands are addressed to them. The sensing devices may be configured to perform different measurement sequences in response to an unaddressed measurement command to minimize interference caused by the sensing devices performing the measurement sequences in parallel.

25 Claims, 15 Drawing Sheets

Related U.S. Application Data which is a continuation of application No. 14/594,674, filed on Jan. 12, 2015, now Pat. No. 9,626,315.

(60) Provisional application No. 62/397,072, filed on Sep. 20, 2016, provisional application No. 61/926,636, filed on Jan. 13, 2014.

(51) Int. Cl.
*H02J 50/10* (2016.01)
*G01N 33/50* (2006.01)

(56) References Cited

U.S. PATENT DOCUMENTS

| | | |
|---|---|---|
| 6,960,987 B2 | 11/2005 | Dohi et al. |
| 9,184,875 B2 | 11/2015 | Sicurello et al. |
| 9,831,985 B2 | 11/2017 | Sicurello et al. |
| 2002/0072785 A1 | 6/2002 | Nelson et al. |
| 2003/0122677 A1 | 7/2003 | Kail, IV |
| 2004/0059396 A1 | 3/2004 | Reinke et al. |
| 2008/0092638 A1 | 4/2008 | Brenneman et al. |
| 2008/0119707 A1 | 5/2008 | Stafford |
| 2008/0154101 A1 | 6/2008 | Jain et al. |
| 2009/0054737 A1 | 2/2009 | Magar et al. |
| 2009/0322557 A1 | 12/2009 | Robb et al. |
| 2010/0073669 A1 | 3/2010 | Colvin, Jr. et al. |
| 2010/0106220 A1 | 4/2010 | Ecker et al. |
| 2010/0230614 A1 | 9/2010 | Lear et al. |
| 2010/0312483 A1 | 12/2010 | Peyser et al. |
| 2011/0034912 A1 | 2/2011 | de Graff et al. |
| 2012/0028820 A1 | 2/2012 | Rhodes et al. |
| 2013/0211213 A1 | 8/2013 | DeHennis et al. |
| 2014/0257059 A1 | 9/2014 | Budiman et al. |
| 2015/0199288 A1 | 7/2015 | DeHennis |

| 50 Hz AC | | | | | | | | | | | | | | |
|---|---|---|---|---|---|---|---|---|---|---|---|---|---|---|
| Time Slot | 0 | 1 | 3 | 5 | 6 | 10 | 11 | 12 | 21 | 30 | 32 | 39 | 45 | 54 | 63 | 65 | 66 | 68 |
| ASIC 1: LED | LEDsOFF | | BLUE LED:ON | | | | | UV LED:ON | | | | LED:OFF | | | | | |
| ASIC 1: Measurement Type | | | 5 | | | | 0 | | | 5 | | 0 | | 2 | | 4 | 9 |
| ASIC 1: Photodiode Channel | | | 1=1 | | | | 2=2 | | | 1=1 | | 2=2 | | | | |
| ASIC 1: Signal Name | | | Blue VLED | | Blue Sigon | | UV Sigon | UV Refon | UV VLED | | Blue Sigoff | | UV Sigoff | UV Refoff | Temperature | | RF | Diagnostic |
| ASIC 1: GainSetMeas | | | 96 | | 107 | | 98 | 82 | 96 | | 107 | | 98 | 82 | 96 | | 96 | 96 |
| ASIC 1: tia_clkoffset | | | 0 | | 0 | | 1 | 1 | 0 | | 0 | | 1 | 1 | 0 | | 0 | 0 |
| ASIC 1: Offset | | | 255=0nA | | 255=0nA | | 255=0nA | 255=0nA | 255=0nA | | 255=0nA | | 255=0nA | 255=0nA | 255=0nA | | 255=0nA | 255=0nA |
| ASIC 1: ADC bits | | | 4-14 | | 4-14 | | 4-14 | 4-14 | 4-14 | | 4-14 | | 4-14 | 4-14 | 4-14 | | 4-14 | 4-14 |

| 60 Hz AC | | | | | | | | | | | | | | |
|---|---|---|---|---|---|---|---|---|---|---|---|---|---|---|
| Time Slot | 0 | 1 | 3 | 5 | 6 | 10 | 11 | 12 | 21 | 30 | 32 | 34 | 38 | 39 | 40 | 49 | 58 | 60 | 61 | 63 |
| ASIC 1: LED | LEDsOFF | | BLUE LED ON | | | | | UV LED ON | | | | LEDs OFF | | | | | |
| ASIC 1: Measurement Type | | | 5 | | | | 0 | | | 5 | | 0 | | 2 | | 4 | 9 |
| ASIC 1: Photodiode Channel | | | 1=1 | | | | 2=2 | | | 1=1 | | 2=2 | | | | |
| ASIC 1: Signal Name | | | Blue VLED | | Blue Sigon | | UV Sigon | UV Refon | UV VLED | | Blue Sigoff | | UV Sigoff | UV Refoff | Temperature | | RF | Diagnostic |
| ASIC 1: GainSetMeas | | | 96 | | 107 | | 98 | 82 | 96 | | 107 | | 98 | 82 | 96 | | 96 | 96 |
| ASIC 1: tia_clkoffset | | | 0 | | 0 | | 1 | 1 | 0 | | 0 | | 1 | 1 | 0 | | 0 | 0 |
| ASIC 1: Offset | | | 255=0nA | | 255=0nA | | 255=0nA | 255=0nA | 255=0nA | | 255=0nA | | 255=0nA | 255=0nA | 255=0nA | | 255=0nA | 255=0nA |
| ASIC 1: ADC bits | | | 4-14 | | 4-14 | | 4-14 | 4-14 | 4-14 | | 4-14 | | 4-14 | 4-14 | 4-14 | | 4-14 | 4-14 |

REMOTELY-POWERED SENSING SYSTEM WITH MULTIPLE SENSING DEVICES

CROSS-REFERENCE TO RELATED APPLICATIONS

The present application claims the benefit of priority to U.S. Provisional Application Ser. No. 62/397,072, filed on Sep. 20, 2016, which is incorporated herein by reference in its entirety. The present application is also a continuation-in-part of U.S. patent application Ser. No. 15/482,141, filed on Apr. 7, 2017, which is a continuation of U.S. patent application Ser. No. 14/594,674, filed on Jan. 12, 2015, now U.S. Pat. No. 9,626,315, which claims the benefit of priority to U.S. Provisional Application Ser. No. 61/926,636, filed on Jan. 13, 2014, both of which are incorporated herein by reference in their entireties.

BACKGROUND

Field of Invention

The present invention relates generally to a sensing system with multiple sensing devices. Specifically, the present invention may relate to a remotely-powered sensing system with multiple sensing devices in an analyte monitoring system.

Discussion of the Background

A conventional implantable analyte sensor may include a single analyte sensing site and an antenna that is inductively coupled to an external transceiver and used solely with the single analyte sensing site. Such a sensor, when implanted, may provide good telemetry coupling with an external transceiver that is worn on the outside of the skin directly over the implanted sensor. However, the sensor only has one analyte sensing site and is dependent upon having an antenna that can receive power and commands from the external transceiver at the same location as the sensing site. These requirements (i.e., only one sensing site and one antenna per sensing site) may limit the range of applications to which the sensor may be applied. There is presently a need in the art for an improved analyte sensor.

SUMMARY

The present invention overcomes the disadvantages of prior systems by providing a sensing system having multiple analyte sensing devices. The sensing system may provide, among other advantages, a single interface device (e.g., antenna or inductive element) that is shared between the multiple analyte sensing devices. The multiple sensing devices may include two or more sensing devices that detect the same analyte (e.g., for secondary, tertiary, or more detection of the analyte) and/or one or more sensing devices that each detect an analyte different than the analyte(s) detected by the other sensing device(s) (e.g., for detection of multiple analytes). In addition, in some embodiments, the multisite sensing system may include a shared communication device (e.g., a two wire interface), which may simplify the overall assembly and form factor.

One aspect of the invention may provide a sensing system. The sensing system may include an interface device, a shared communication device, a first analyte sensing device, and a second analyte sensing device. The shared communication device may be connected to the interface device. The first analyte sensing device may be connected to the shared communication device and may be configured to perform a first measurement sequence in response to receiving an unaddressed measurement command via the interface device and the shared communication device. The second analyte sensing device may be connected to the shared communication device and may be configured to perform a second measurement sequence in response to receiving the unaddressed measurement command via the interface device and the shared communication device, wherein the first and second measurement sequences are different.

In some embodiments, the sensing system may include a third analyte sensing device connected to the shared communication device and configured to perform a third measurement sequence in response to receiving the unaddressed measurement command via the interface device and the shared communication device, and the third measurement sequence may be different than the first and second measurement sequences.

In some embodiments, the first analyte sensing device may be configured to perform the first measurement sequence at the same time that the second analyte sensing device performs the second measurement sequence. In some embodiments, the first measurement sequence may be configured to turn a light source of the first sensing device on at times different from times at which the second measurement sequence turns a light source of the second sensing device on.

In some embodiments, the first analyte sensing device may be configured to: receive an addressed measurement command via the interface device and the shared communication device; determine whether the addressed measurement command is addressed to the first analyte sensing device; if the addressed measurement command is determined to be addressed to the first analyte sensing device, perform a measurement sequence; and, if the addressed measurement command is determined to be not addressed to the first analyte sensing device, not perform a measurement sequence in response to the addressed measurement command. In some embodiments, the measurement sequence performed by the first analyte sensing device in response to the addressed measurement command may be the first measurement sequence.

In some embodiments, the first analyte sensing device may be configured to: receive an addressed read measurement data command via the interface device and the shared communication device; determine whether the addressed read measurement data command is addressed to the first analyte sensing device; if the addressed read measurement data command is determined to be addressed to the first analyte sensing device, convey measurement data via the shared communication device and interface device; and, if the addressed read measurement data command is determined to be not addressed to the first analyte sensing device, not convey measurement data in response to the addressed read measurement data command.

In some embodiments, the first analyte sensing device comprises a light source, and the first measurement sequence comprises measuring one or more characteristics of the light source. In some embodiments, the interface device is an inductive element. In some embodiments, the sensing system may further include a sensor housing, and the interface device, shared communication device, and first and second analyte sensing devices may be contained within the sensor housing. In some embodiments, the shared communication device comprises shared wires.

Another aspect of the invention may provide a method including receiving an unaddressed measurement command at first and second analyte sensing devices of a sensing system via an interface device and shared communication device of the sensing system. The method may include using the first analyte sensing device to perform a first measurement sequence in response to receiving the unaddressed measurement command. The method may include using the second analyte sensing device to perform a second measurement sequence in response to receiving the addressed measurement command, wherein the first and second measurement sequences are different.

In some embodiments, the method may include receiving the unaddressed measurement command at a third analyte sensing devices of the sensing system via the interface device and the shared communication device of the sensing system, and using the third analyte sensing device to perform a third measurement sequence in response to receiving the unaddressed measurement command, wherein the third measurement sequence is different than the first and second measurement sequences. In some embodiments, the first analyte sensing device may be configured to perform the first measurement sequence at the same time that the second analyte sensing device performs the second measurement sequence. In some embodiments, using the first analyte sensing device to perform the first measurement sequence comprises turning a light source of the first analyte sensing device on at times different from times at which the second measurement sequence turns a light source of the second sensing device on.

In some embodiments, the method may include receiving an addressed measurement command at the first and second analyte sensing devices of the sensing system via the interface device and the shared communication device of the sensing system. The method may include using the first analyte sensing device to determine whether the addressed measurement command is addressed to the first analyte sensing device. The method may include using the first analyte sensing device to perform a measurement sequence in response to the addressed measurement command if the first analyte sensing device determines that the addressed measurement command is addressed to the first analyte sensing device, wherein the first analyte sensing device does not perform a measurement sequence in response to the addressed measurement command if the first analyte sensing device determines that the addressed measurement command is not addressed to the first analyte sensing device. The method may include using the second analyte sensing device to determine whether the addressed measurement command is addressed to the second analyte sensing device. The method may include using the second analyte sensing device to perform a measurement sequence in response to the addressed measurement command if the second analyte sensing device determines that the addressed measurement command is addressed to the second analyte sensing device. The second analyte sensing device may not perform a measurement sequence in response to the addressed measurement command if the second analyte sensing device determines that the addressed measurement command is not addressed to the second analyte sensing device. In some embodiments, the measurement sequence performed by the first analyte sensing device in response to the addressed measurement command may be the first measurement sequence, and the measurement sequence performed by the second analyte sensing device in response to the addressed measurement command may be the second measurement sequence.

In some embodiments, the method may include receiving an addressed read measurement data command at the first and second analyte sensing devices of the sensing system via the interface device and the shared communication device of the sensing system. The method may include using the first analyte sensing device to determine whether the addressed read measurement data command is addressed to the first analyte sensing device. The method may include using the first analyte sensing device to convey measurement data if the first analyte sensing device determines that the addressed read measurement data command is addressed to the first analyte sensing device. The first analyte sensing device may not convey measurement data if the first analyte sensing device determines that the addressed read measurement data command is not addressed to the first analyte sensing device. The method may include using the second analyte sensing device to determine whether the addressed read measurement data command is addressed to the second analyte sensing device. The method may include using the second analyte sensing device to convey measurement data if the second analyte sensing device determines that the addressed read measurement data command is addressed to the second analyte sensing device. The second analyte sensing device may not convey measurement data if the second analyte sensing device determines that the addressed read measurement data command is not addressed to the second analyte sensing device.

In some embodiments, using the first analyte sensing device to perform the first measurement sequence may include measuring one or more characteristics of a light source of the first analyte sensing device. In some embodiments, the interface device may be an inductive element.

Still another aspect of the invention may provide a sensing system including an interface device, a shared communication device, a first analyte sensing device, and a second analyte sensing device. The shared communication device may be connected to the interface device. The first analyte sensing device may be connected to the shared communication device. The first analyte sensing device may be configured to receive an unaddressed measurement command via the interface device and the shared communication device. The first analyte sensing device may be configured to perform a measurement sequence in response to receiving the unaddressed measurement command. The first analyte sensing device may be configured to receive an addressed read measurement data command via the interface device and the shared communication device. The first analyte sensing device may be configured to determine whether the addressed read measurement data command is addressed to the first analyte sensing device. The first analyte sensing device may be configured to, if the addressed read measurement data command is determined to be addressed to the first analyte sensing device, convey measurement data via the shared communication device and interface device. The first analyte sensing device may be configured to, if the addressed read measurement data command is determined to be not addressed to the first analyte sensing device, not convey measurement data in response to the addressed read measurement data command. The second analyte sensing device may be connected to the shared communication device. The second analyte sensing device may be configured to receive the unaddressed measurement command via the interface device and the shared communication device. The second analyte sensing device may be configured to perform a measurement sequence in response to receiving the unaddressed measurement command. The second analyte sensing device may be configured to receive the addressed read measurement data command via the interface device and the shared communication device. The second analyte sensing device may be configured to determine whether the addressed read measurement data command is addressed to the second analyte sensing device. The second analyte sensing device may be configured to, if the addressed read measurement data command is determined to be addressed to the second analyte sensing device, convey measurement data via the shared communication device and interface device. The second analyte sensing device may be configured to, if the addressed read measurement data command is determined to be not addressed to the second analyte sensing device, not convey measurement data in response to the addressed read measurement data command.

In some embodiments, the sensing system may further include a third analyte sensing device connected to the shared communication device. The sensing system may be configured to receive the unaddressed measurement command via the interface device and the shared communication device. The sensing system may be configured to perform a measurement sequence in response to receiving the unaddressed measurement command. The sensing system may be configured to receive the addressed read measurement data command via the interface device and the shared communication device. The sensing system may be configured to determine whether the addressed read measurement data command is addressed to the third analyte sensing device. The sensing system may be configured to, if the addressed read measurement data command is determined to be addressed to the third analyte sensing device, convey measurement data via the shared communication device and interface device. The sensing system may be configured to, if the addressed read measurement data command is determined to be not addressed to the third analyte sensing device, not convey measurement data in response to the addressed read measurement data command. In some embodiments, the shared communication device comprises shared wires.

Yet another aspect of the invention may provide a method including receiving an unaddressed measurement command at first and second analyte sensing devices of a sensing system via an interface device and shared communication device of the sensing system. The method may include using the first analyte sensing device to perform a measurement sequence in response to receiving the unaddressed measurement command. The method may include using the second analyte sensing device to perform a measurement sequence in response to receiving the addressed measurement command. The method may include receiving an addressed read measurement data command at the first and second analyte sensing devices of the sensing system via the interface device and the shared communication device of the sensing system. The method may include using the first analyte sensing device to determine whether the addressed read measurement data command is addressed to the first analyte sensing device. The method may include using the first analyte sensing device to convey measurement data if the first analyte sensing device determines that the addressed read measurement data command is addressed to the first analyte sensing device. The first analyte sensing device may not convey measurement data if the first analyte sensing device determines that the addressed read measurement data command is not addressed to the first analyte sensing device. The method may include using the second analyte sensing device to determine whether the addressed read measurement data command is addressed to the second analyte sensing device. The method may include using the second analyte sensing device to convey measurement data if the second analyte sensing device determines that the addressed read measurement data command is addressed to the second analyte sensing device. The second analyte sensing device may not convey measurement data if the second analyte sensing device determines that the addressed read measurement data command is not addressed to the second analyte sensing device.

In some embodiments, the method may further include receiving the unaddressed measurement command at a third analyte sensing devices of the sensing system via the interface device and the shared communication device of the sensing system. The method may further include using the third analyte sensing device to perform a measurement sequence in response to receiving the unaddressed measurement command. The method may further include receiving the addressed read measurement data command at the third analyte sensing device of the sensing system via the interface device and the shared communication device of the sensing system. The method may further include using the third analyte sensing device to determine whether the addressed read measurement data command is addressed to the third analyte sensing device. The method may further include using the third analyte sensing device to convey measurement data if the third analyte sensing device determines that the addressed read measurement data command is addressed to the third analyte sensing device. The third analyte sensing device may not convey measurement data if the third analyte sensing device determines that the addressed read measurement data command is not addressed to the third analyte sensing device.

Still another aspect of the invention may provide a transceiver including a sensor interface device, and a controller. The controller may be configured to convey an unaddressed measurement command to a transceiver interface device of a sensing system via the sensor interface device. The controller may be configured to convey a first addressed read measurement data command to the transceiver interface device of the sensing system via the sensor interface device. The first addressed read measurement data command may be addressed to a first sensing device of the sensing system. The controller may be configured to receive measurement data from the first sensing device of the sensing system via the transceiver interface device of the sensing system and the sensor interface device. The controller may be configured to convey a second addressed read measurement data command to the transceiver interface device of the sensing system via the sensor interface device. The second addressed read measurement data command may be addressed to a second sensing device of the sensing system. The controller may be configured to receive measurement data from the second sensing device of the sensing system via the transceiver interface device of the sensing system and the sensor interface device.

In some embodiments, the controller may be further configured to convey a turn-off command to the transceiver interface device of the sensing system via the sensor interface device. The turn-off command may be addressed to one of the first and second sensing devices of the sensing system, and the turn-off command may be configured to cause the one of the first and second sensing devices to not respond to unaddressed measurement commands. In some embodiments, the controller may further configured to convey a third addressed read measurement data command to the transceiver interface device of the sensing system via the sensor interface device, and the third addressed read measurement data command may be addressed to a third sensing device of the sensing system. In some embodiments, the controller may further configured to receive measurement data from the third sensing device of the sensing system via the transceiver interface device of the sensing system and the sensor interface device.

In some embodiments, the sensor interface device may be an inductive element, and the transceiver interface device may be an inductive element. In some embodiments, the controller may be further configured to measure a strength of coupling of the sensor interface device of the transceiver and the transceiver interface device of the sensing system within an electrodynamic field. In some embodiments, the controller may be further configured to: compare the measured strength of coupling to a threshold, and convey the unaddressed measurement command to the transceiver interface device of the sensing system only if the measured strength of coupling is above the threshold. In some embodiments, the controller may be further configured to, if the measured strength of coupling is above the threshold: convey a first addressed measurement command to the transceiver interface device of the sensing system via the sensor interface device, wherein the first addressed measurement command is addressed to the first sensing device of the sensing system, and convey a second addressed measurement command to the transceiver interface device of the sensing system via the sensor interface device, wherein the second addressed measurement command is addressed to the second sensing device of the sensing system.

Yet another aspect of the invention may provide a method for conveying commands to sensing system including first and second sensing devices. The method may include using a controller of a transceiver to convey an unaddressed measurement command to a transceiver interface device of a sensing system via a sensor interface device of the transceiver. The method may include using a controller of a transceiver to convey a first addressed read measurement data command to the transceiver interface device of the sensing system via the sensor interface device of the transceiver, wherein the first addressed read measurement data command is addressed to a first sensing device of the sensing system. The method may include using a controller of a transceiver to receive measurement data from the first sensing device of the sensing system via the transceiver interface device of the sensing system and the sensor interface device of the transceiver. The method may include using a controller of a transceiver to convey a second addressed read measurement data command to the transceiver interface device of the sensing system via the sensor interface device. The second addressed read measurement data command may be addressed to a second sensing device of the sensing system. The method may include using a controller of a transceiver to receive measurement data from the second sensing device of the sensing system via the transceiver interface device of the sensing system and the sensor interface device of the transceiver.

In some embodiments, the method may further include using the controller of the transceiver to convey a turn-off command to the transceiver interface device of the sensing system via the sensor interface device. The turn-off command may be addressed to one of the first and second sensing devices of the sensing system, and the turn-off command may be configured to cause the one of the first and second sensing devices to not respond to unaddressed measurement commands. In some embodiments, the method may further include using the controller of the transceiver to: convey a third addressed read measurement data command to the transceiver interface device of the sensing system via the sensor interface device of the transceiver, wherein the third addressed read measurement data command is addressed to a third sensing device of the sensing system, and receive measurement data from the third sensing device of the sensing system via the transceiver interface device of the sensing system and the sensor interface device of the transceiver.

In some embodiments, the sensor interface device may be an inductive element, the transceiver interface device may be an inductive element, and the method may further include using the controller of the transceiver to measure a strength of coupling of the sensor interface device of the transceiver and the transceiver interface device of the sensing system within an electrodynamic field. In some embodiments, the method may further include using the controller of the transceiver to: compare the measured strength of coupling to a threshold, and convey the unaddressed measurement command to the transceiver interface device of the sensing system only if the measured strength of coupling is above the threshold. In some embodiments, the method may further include, if the measured strength of coupling is above the threshold, using the controller of the transceiver to: convey a first addressed measurement command to the transceiver interface device of the sensing system via the sensor interface device, and convey a second addressed measurement command to the transceiver interface device of the sensing system via the sensor interface device. The first addressed measurement command may be addressed to the first sensing device of the sensing system, and the second addressed measurement command may be addressed to the second sensing device of the sensing system.

Still another aspect of the invention may provide a transceiver including a sensor interface device and a controller. The controller may be configured to cause first and second sensing devices of a sensing system to perform measurement sequences by conveying one or more measurement commands to a transceiver interface device of the sensing system via the sensor interface device. The controller may be configured to receive first measurement data from the first sensing device of the sensing system via the sensor interface device. The controller may be configured to receive second measurement data from the second sensing device of the sensing system via the sensor interface device. The controller may be configured to calculate a first analyte concentration using the received first measurement data. The controller may be configured to calculate a second analyte concentration using the received second measurement data. The controller may be configured to apply a first weighting to the first analyte concentration. The controller may be configured to apply a second weighting to the second analyte concentration. The controller may be configured to calculate a combined analyte concentration using the weighted first and second analyte concentrations. The controller may be configured to detect a first degradation of a performance of the first sensing device. The controller may be configured to detect a second degradation of a performance of the second sensing device. The controller may be configured to adjust the first and second weightings using the detected first and second degradations.

In some embodiments, the controller may be configured to cause the first and second sensing devices to perform the measurement sequences by conveying an unaddressed measurement command to the transceiver interface device of the sensing system via the sensor interface device. In some embodiments, the controller may be configured to convey the combined analyte concentration to a display device. In some embodiments, the controller may be configured to determine whether the first and second analyte concentrations are in agreement. In some embodiments, the controller may be configured to determine whether the first sensing device is trustworthy by analyzing the first analyte concentration and one or more previous analyte concentrations calculated using measurement data received from the first sensing device of the sensing system via the sensor interface device and determining whether a trustworthy data pattern exists.

Yet another aspect of the invention may provide a method including using a controller of a transceiver to cause first and second sensing devices of a sensing system to perform measurement sequences by conveying one or more measurement commands to a transceiver interface device of the sensing system via a sensor interface device of the transceiver. The method may include using a controller of a transceiver to receive first measurement data from the first sensing device of the sensing system via the sensor interface device of the transceiver. The method may include using a controller of a transceiver to receive second measurement data from the second sensing device of the sensing system via the sensor interface device of the transceiver. The method may include using a controller of a transceiver to calculate a first analyte concentration using the received first measurement data. The method may include using a controller of a transceiver to calculate a second analyte concentration using the received second measurement data. The method may include using a controller of a transceiver to apply a first weighting to the first analyte concentration. The method may include using a controller of a transceiver to apply a second weighting to the second analyte concentration. The method may include using a controller of a transceiver to calculate a combined analyte concentration using the weighted first and second analyte concentrations. The method may include using a controller of a transceiver to detect a first degradation of a performance of the first sensing device. The method may include using a controller of a transceiver to detect a second degradation of a performance of the second sensing device. The method may include using a controller of a transceiver to adjust the first and second weightings using the detected first and second degradations.

In some embodiments, using the controller to cause the first and second sensing devices to perform the measurement sequences may include conveying an unaddressed measurement command to the transceiver interface device of the sensing system via the sensor interface device. In some embodiments, the method may further include using the controller to convey the combined analyte concentration to a display device. In some embodiments, the method may further include using the controller to determine whether the first and second analyte concentrations are in agreement. In some embodiments, the method may further include using the controller to determine whether the first sensing device is trustworthy by analyzing the first analyte concentration and one or more previous analyte concentrations calculated using measurement data received from the first sensing device of the sensing system via the sensor interface device and determining whether a trustworthy data pattern exists.

These and other embodiments encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 11 are tables illustrating measurement sequences performed by first and second sensing devices of a sensing system embodying aspects of the present invention.

FIG. 12 are tables illustrating measurement sequences optimized for parallel performance by first and second sensing devices of a sensing system embodying aspects of the present invention.

DETAILED DESCRIPTION OF PREFERRED EMBODIMENTS

Figure 1:
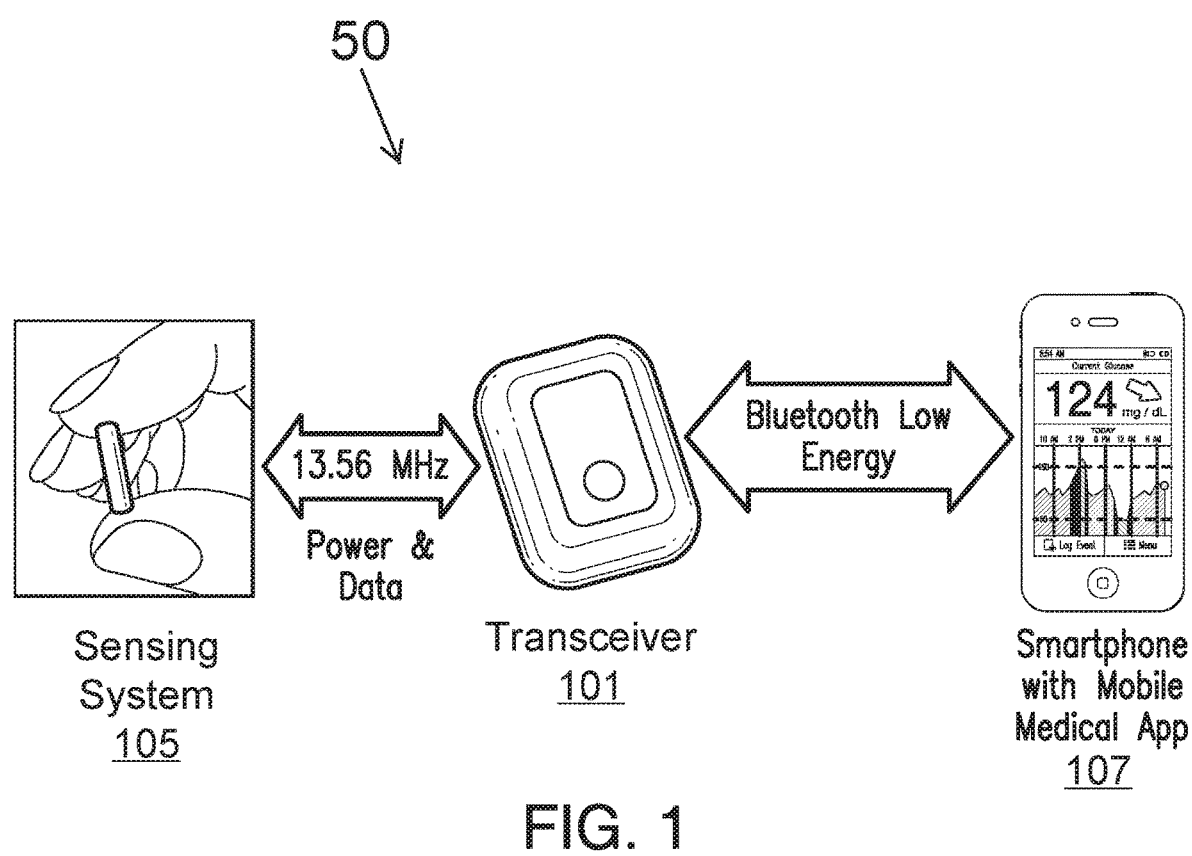
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensing system 105, a transceiver 101, and a display device 107. In some embodiments, the sensing system 105 may be a small, fully subcutaneously implantable sensing system that measures the amount or concentration of an analyte (e.g., glucose) in a medium (e.g., interstitial fluid) of a living animal (e.g., a living human). However, this is not required, and, in some alternative embodiments, the sensing system 105 may be a partially implantable (e.g., transcutaneous) sensing system or a fully external sensing system. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensing system 105 via one or more wired connections. In some non-limiting embodiments, the transceiver 101 may be a smartphone (e.g., an NFC-enabled smartphone). In some embodiments, the transceiver 101 may communicate information (e.g., one or more analyte measurements) wirelessly (e.g., via a Bluetooth™ communication standard such as, for example and without limitation Bluetooth Low Energy) to a hand held application running on a display device 107 (e.g., smartphone).

Figure 2:
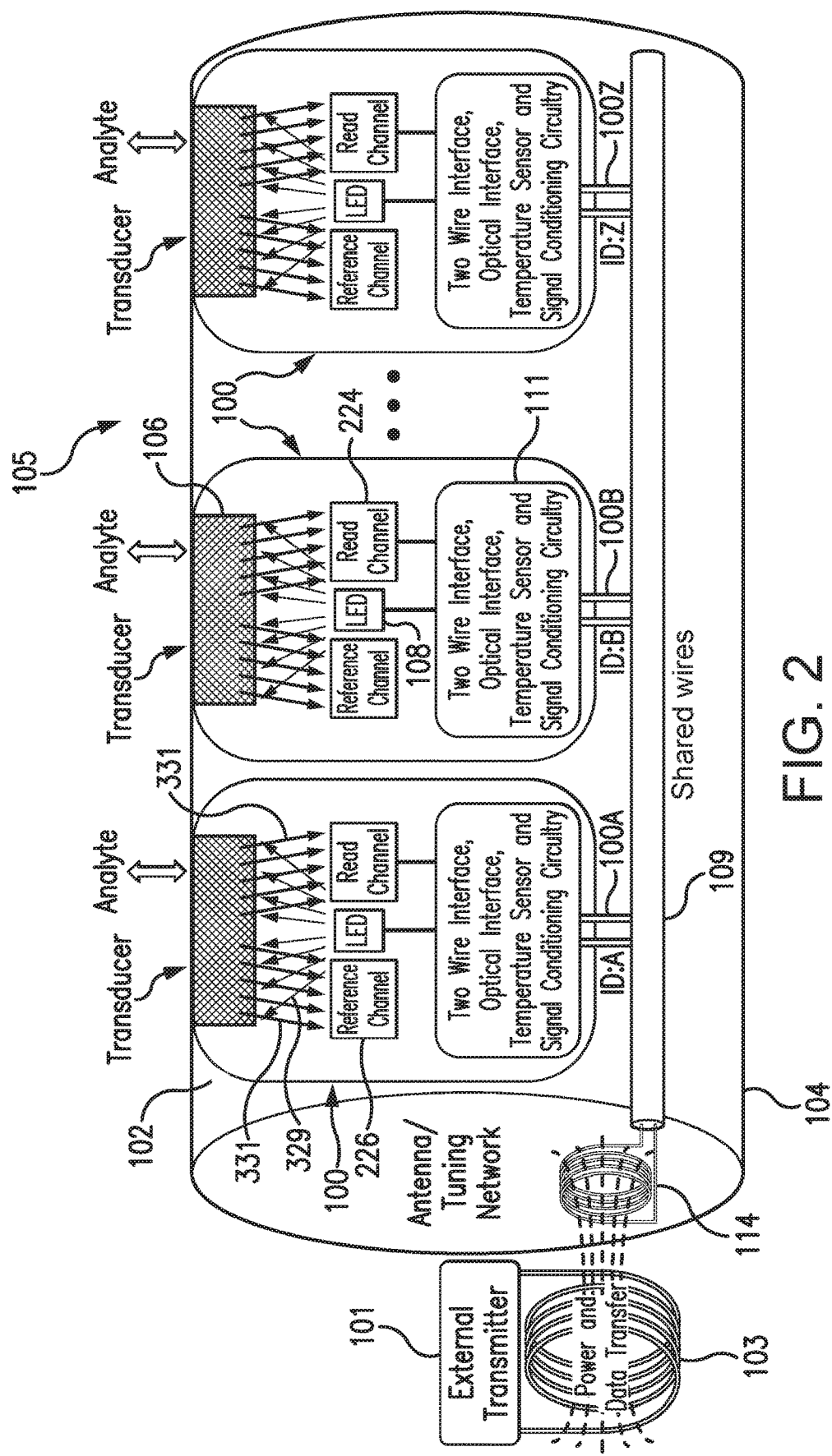
FIG. 2 is a schematic view illustrating a sensing system embodying aspects of the present invention.
Figure 3:
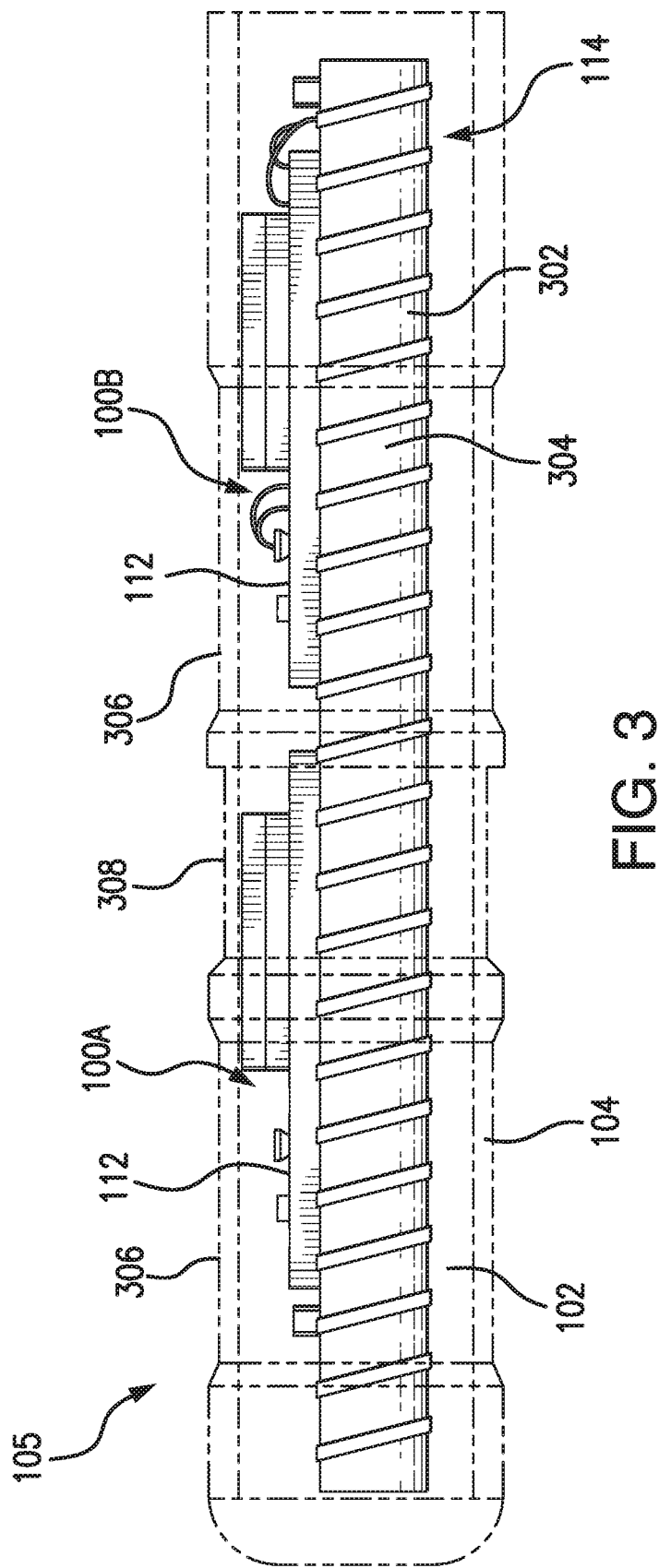
FIG. 3 is a side view illustrating a sensing system embodying aspects of the present invention.

FIGS. 2 and 3 are schematic and side views, respectively, of an analyte sensing system 105 embodying aspects of the present invention. As illustrated in FIG. 2, the sensing system 105 may include two or more analyte sensing devices 100. For example, in the embodiment illustrated in FIG. 2, the sensing system 105 includes sensing devices 100A, 100B, and 100Z, but the sensing system 105 may include any number of sensing devices 100 greater than or equal to two (e.g., two, three, four, five, ten, etc.). FIG. 3 illustrates an embodiment in which the sensing system 105 includes two sensing devices 100A and 100B.

The analyte sensing devices 100 may detect the presence, amount, and/or concentration of an analyte (e.g., glucose, oxygen, cardiac markers, low-density lipoprotein (LDL), high-density lipoprotein (HDL), or triglycerides). In some embodiments, two or more of the sensing devices 100 may detect the same analyte. In some non-limiting embodiments where two or more of the sensing devices 100 detect the same analyte, a voting scheme (e.g., taking an integrated average of the measurements from the sensing devices detecting the same analyte and/or discounting a measurement that is significantly different than other measurements of the same analyte) may be used (e.g., by the transceiver 101). In some embodiments, one or more of the sensing device 100 may detect a first analyte, and another one or more sensing devices 100 may detect a second, different analyte. In some embodiments, sensing devices 100 may additionally detect third, fourth, and/or more different analytes. In some embodiments, the sensing devices 100 are spatially separated for analyte detection at multiple locations. In some non-limiting embodiments, the analyte sensing devices 100 may be optical sensors (e.g., fluorometers). In some embodiments, the sensing devices 100 may be chemical or biochemical sensors.

The sensing system 105 may communicate with the external transceiver 101. The transceiver 101 may be an electronic device that communicates with the multisite sensing system 105 to power the sensing devices 100 and/or receive measurement data (e.g., photodetector and/or temperature sensor readings) from the sensing devices 100. The measurement data may include one or more readings from one or more photodetectors of the sensing devices 100 and/or one or more readings from one or more temperature sensors of the sensing devices 100. In some embodiments, the transceiver 101 may calculate analyte concentrations from the measurement data received from the sensing devices 100. However, it is not required that the transceiver 101 perform the analyte concentration calculations itself, and, in some alternative embodiments, the transceiver 101 may instead convey/relay the measurement data received from the sensing devices 100 to another device for calculation of analyte concentrations.

In some embodiments (e.g., embodiments in which the sensing system 105 is a fully implantable sensing system), the transceiver 101 may implement a passive telemetry for communicating with the implantable sensing system 105 via an inductive magnetic link for both power and data transfer. The sensing system 105 may include an inductive element 114, which may be, for example, a ferrite based microantenna. In some embodiments, as shown in FIG. 3, the inductive element 114 may include a conductor 302 in the form of a coil and a magnetic core 304. In some non-limiting embodiments, the core 304 may be, for example and without limitation, a ferrite core. In some embodiments, the inductive element 114 may be connected to analyte detection circuitry of the sensing devices 100. For example, in some embodiments, where the sensing devices 100 are optical sensors, the inductive element 114 may be connected to micro-fluorimeter circuitry (e.g., an application specification integrated circuit (ASIC)) and a related optical detection system of the sensing device 100. In some embodiments, the sensing system 105 may not include a battery, and, as a result, the sensing system 105 may rely on the transceiver 101 to provide power for the sensing devices 100 of the sensor system 105 and a data link to convey analyte-related data from the sensing devices 100 to transceiver 101.

In some non-limiting embodiments, the sensing system 105 may be a passive, fully implantable multisite sensing system having a small size. For a sensing system 105 that is a fully implantable sensing system having no battery power source, the transceiver 101 may provide energy to run the sensing devices 100 of the sensing system 105 via a magnetic field. In some embodiments, the magnetic transceiver-sensing system link can be considered as "weakly coupled transformer" type. The magnetic transceiver-sensing system link may provide energy and a link for data transfer using amplitude modulation (AM). Although in some embodiments, data transfer is carried out using AM, in alternative embodiments, other types of modulation may be used. The magnetic transceiver-sensor link may have a low efficiency of power transfer and, therefore, may require relatively high power amplifier to energize the sensing devices 100 of the sensing system 105 at longer distances. In some non-limiting embodiments, the transceiver 101 and sensing system 105 may communicate using near field communication (e.g., at a frequency of 13.56 MHz, which can achieve high penetration through the skin and is a medically approved frequency band) for power transfer. However, this is not required, and, in other embodiments, different frequencies may be used for powering and communicating with the sensor 100.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensing system 105, which powers the sensing devices 100. The transceiver 101 may also convey data (e.g., commands) to the sensing devices 100 of the sensing system 105. For example, in a non-limiting embodiment, the transceiver 101 may convey data by modulating the electromagnetic wave used to power the sensing devices 100 (e.g., by modulating the current flowing through a coil 103 of the transceiver 101). The modulation in the electromagnetic wave generated by the transceiver 101 may be detected/extracted by the sensing devices 100. Moreover, the transceiver 101 may receive data (e.g., measurement information) from the sensing devices 100 of the sensing system 105. For example, in a non-limiting embodiment, the transceiver 101 may receive data by detecting modulations in the electromagnetic wave generated by one or more of the sensing devices 100, e.g., by detecting modulations in the current flowing through the coil 103 of the transceiver 101.

The inductive element 103 of the transceiver 101 and the inductive element 114 of the sensing system 105 may be in any configuration that permits adequate field strength to be achieved when the two inductive elements are brought within adequate physical proximity.

In some embodiments, as shown in FIG. 2, the sensing system 105 may include a shared communication device 109 connected to the inductive element 114 and to each of the sensing devices 100. In some embodiments, the shared communication device 109 may be shared wires. In some non-limiting embodiments, the shared communication device 109 may be two wires. For example, in one non-limiting embodiment, the shared communication device 109 may consist of two wires connected to the inductive element 114. A first wire of the shared communication device 109 may be connected to a first end of the inductive element 114 and to a first input/output port (e.g., a pin) of each of the sensing devices 100, and a second wire of the shared communication device 109 may be connected to a second end of the inductive element 114 and to a second input/output port (e.g., a pin) of each of the sensing devices 100. In some non-limiting embodiments, the first and second input/output ports may be resonant nodes of an LC tank circuit. In some embodiments, the shared communication device 109 may deliver the power generated by the inductive element 114 to each of the sensing devices 100. In some embodiments, the connection of the shared communication device 109 to the inductive element 114 may facilitate data communication between the sensing devices 100 and the transceiver 101.

In some non-limiting embodiments, the sensing devices 100 may include address mode communication features (e.g., address mode communication features of bus interface circuitry included in the circuit components 111 of the sensing devices 100). In some embodiments, some commands (e.g., measurement or read commands) conveyed by the inductive element 103 of the transceiver 101 (e.g., by modulating the electromagnetic wave) may include an address (e.g., a unique sensor ID) identifying a particular one of the sensing devices 100, and the address mode communication features of the sensing devices 100 may extract the address in the conveyed addressed commands. In some embodiments, only the sensor 100 to which the command is addressed (e.g., only the sensing device 100 whose unique ID matches the unique ID included in the command) performs the command and provides a response through the passive interface (e.g., by modulating in the electromagnetic wave). Although one example for operation of the sensing devices 100 is provided above, alternative embodiments may achieve addressed sensor operation in one or more different fashions. For example, in some alternative embodiments, the sensing devices 100 may be configured to use an anti-collision algorithm for responding on the shared antenna 114. In some non-limiting embodiments, the shared communication device 109 may enable the single inductive element 114 (e.g., a single antenna) to interface with multiple sensing devices 100, which may be spatially separated for analyte detection/transduction at multiple locations.

In some non-limiting embodiments, as illustrated in FIGS. 2 and 3, the sensing devices 100, shared communication device 109, and inductive element 114 may be encased in a system housing 104 (i.e., body, shell, capsule, or encasement), which may be rigid and biocompatible. In one non-limiting embodiment, the system housing 104 may be a silicon tube. However, this is not required, and, in other embodiments, different materials and/or shapes may be used for the system housing 104.

In some embodiments, as shown in FIGS. 2 and 3, the sensing system 105 may include a transmissive optical cavity 102. In some non-limiting embodiments, the transmissive optical cavity 102 may be formed from a suitable, optically transmissive polymer material, such as, for example, acrylic polymers (e.g., polymethylmethacrylate (PMMA)). However, this is not required, and, in other embodiments, different materials may be used for the transmissive optical cavity 102.

In some embodiments, as shown in FIG. 2, the sensing devices 100 may each include an analyte indicator element 106, such as, for example, a polymer graft coated, diffused, adhered, or embedded on or in at least a portion of the exterior surface of the system housing 104. In some non-limiting embodiments, as shown in FIG. 3, the system housing 104 may include one or more cutouts or recesses 306, and the analyte indicator elements 106 may be located (partially or entirely) in the cutouts 306. The analyte indicator element 106 (e.g., polymer graft) of the sensor 100 may include indicator molecules (e.g., fluorescent indicator molecules) exhibiting one or more detectable properties (e.g., optical properties) based on the amount or concentration of the analyte in proximity to the analyte indicator element.

In some embodiments, as shown in FIG. 2, the sensing devices 100 may each include one or more light sources 108 that emit excitation light 329 over a range of wavelengths that interact with the indicator molecules in the analyte indicator element 106. The sensing devices 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules of the analyte indicator element 106 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflected excitation light) and reflect the remaining wavelengths.

In some non-limiting embodiments, the sensing devices 100 may include a temperature transducer. In some non-limiting embodiments, the multisite sensing system 105 may include one or more drug-eluting polymer matrixes that disperse one or more therapeutic agents (e.g., an anti-inflammatory drug). In some embodiments, as shown in FIG. 3, the system housing 104 may include one or more cutouts or recesses 308, and the one or more drug-eluting polymer matrixes may be located (partially or entirely) in the cutouts 308.

In some embodiments, the sensing devices 100 may include circuit components 111. In some non-limiting embodiments, the circuit components 111 may include a bus interface, optical interface, temperature sensor, analog-to-digital converter, and/or signal conditioning circuitry. In some non-limiting embodiments, the bus interface may perform the address mode communication described above. In some of these address mode communication embodiments, all of the sensing devices 100 may receive an addressed command, and only the sensor 100 to which the command is addressed responds to the command via the bus 109 and shared inductive element 114. In some embodiments, the all of the sensing devices 100 may receive unaddressed commands, and all of the sensing devices 100 may respond to the unaddressed commands.

In some embodiments, as shown in FIG. 3, the sensing devices 100 may each include a substrate 112. In some non-limiting embodiments, as illustrated in FIG. 3, the substrate 112 of each sending device 100 may be attached to the inductive element 114. In some embodiments, the substrate 112 may be a circuit board (e.g., a printed circuit board (PCB) or flexible PCB) on which one or more of the circuit components 111 (e.g., analog and/or digital circuit components) may be mounted or otherwise attached. However, in some alternative embodiments, the substrate 112 may be a semiconductor substrate having one or more of the circuit components 111 fabricated therein. For instance, the fabricated circuit components may include analog and/or digital circuitry. Also, in some embodiments in which the substrate 112 is a semiconductor substrate, in addition to the circuit components fabricated in the semiconductor substrate, circuit components may be mounted or otherwise attached to the semiconductor substrate. In other words, in some semiconductor substrate embodiments, a portion or all of the circuit components 111, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components 111 is secured to the semiconductor substrate, which may provide communication paths between the various secured components.

Figure 4:
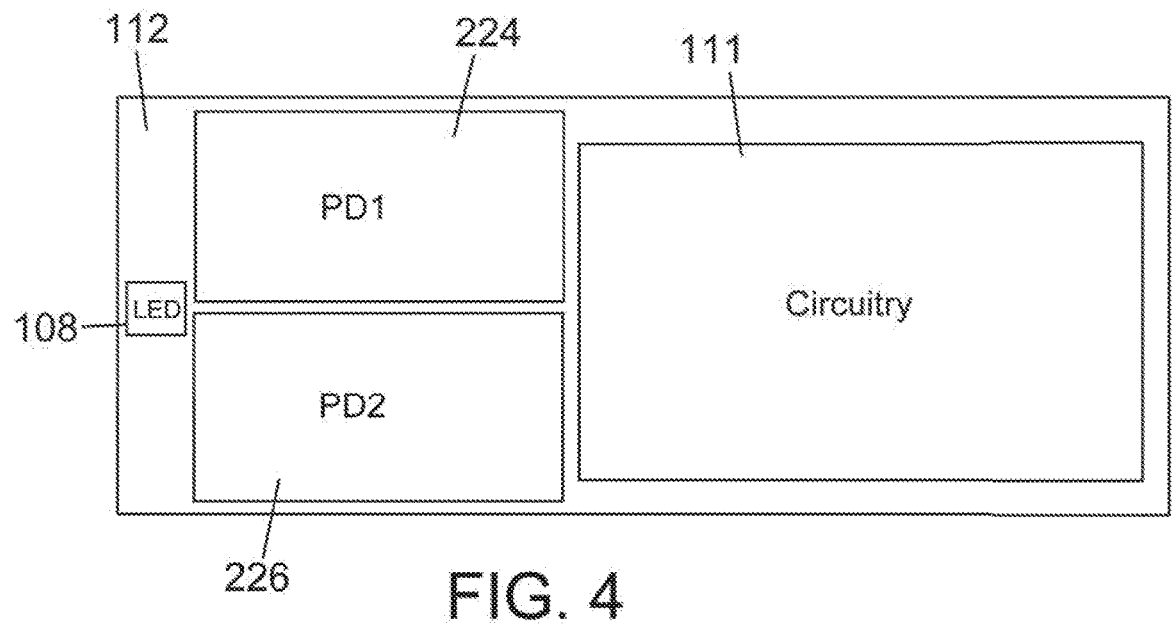
FIG. 4 is a schematic view illustrating the layout of a semiconductor substrate of a sensor system embodying aspects of the present invention.
Figure 5:
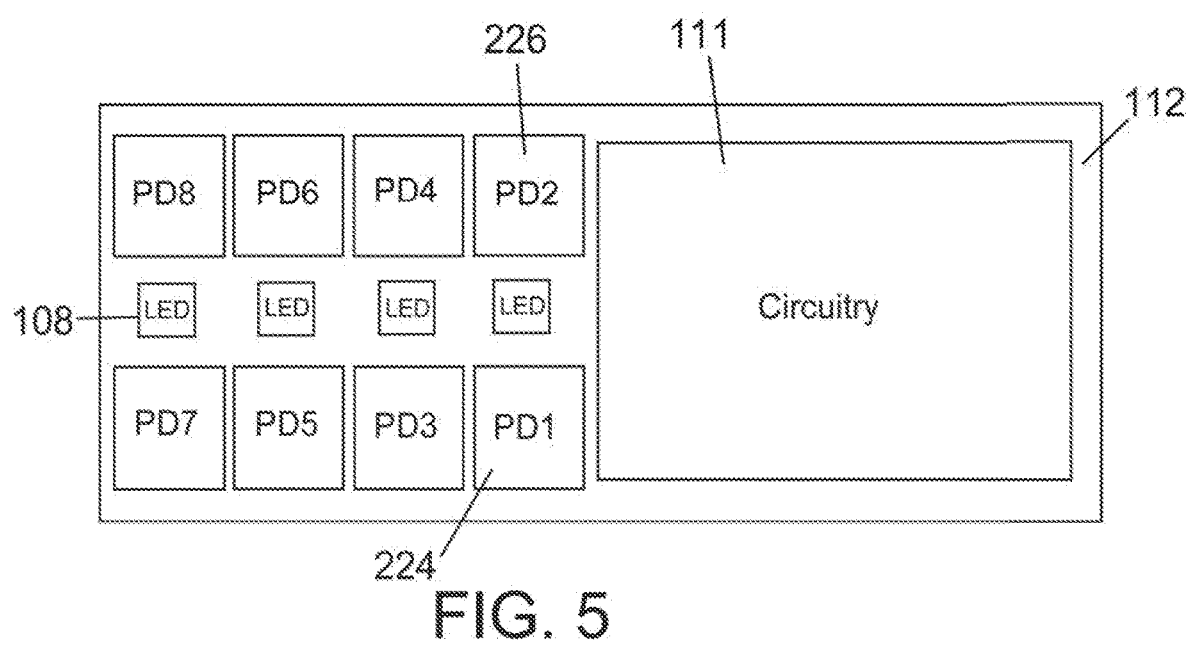
FIG. 5 is a schematic view illustrating the layout of a semiconductor substrate of a sensor system embodying aspects of the present invention.

In some embodiments, each of the sensing devices 100 may include one or more light sources 108, and the one or more light sources 108 may be mounted on or fabricated within in the substrate 112. In some embodiments, each of the sensing devices 100 may include one or more photodetectors 224, 226, and the one or more photodetectors 224, 226 may be mounted on or fabricated within in the substrate 112. In some non-limiting embodiments, one or more light sources 108 may be mounted on the substrate 112, one or more photodetectors may be fabricated within the substrate 112, and all or a portion of the circuit components 111 may be fabricated within the substrate 112. FIG. 4 illustrates a non-limiting example of the layout of a substrate 112 of a sensing device 100 having one light source 108, two photodetectors PD1, PD2, and circuit components 111. FIG. 5 illustrates a non-limiting example of the layout of a substrate 112 of a sensing device 100 having four light sources 108, eight photodetectors PD1-PD8, and circuit components 111.

Figure 6:
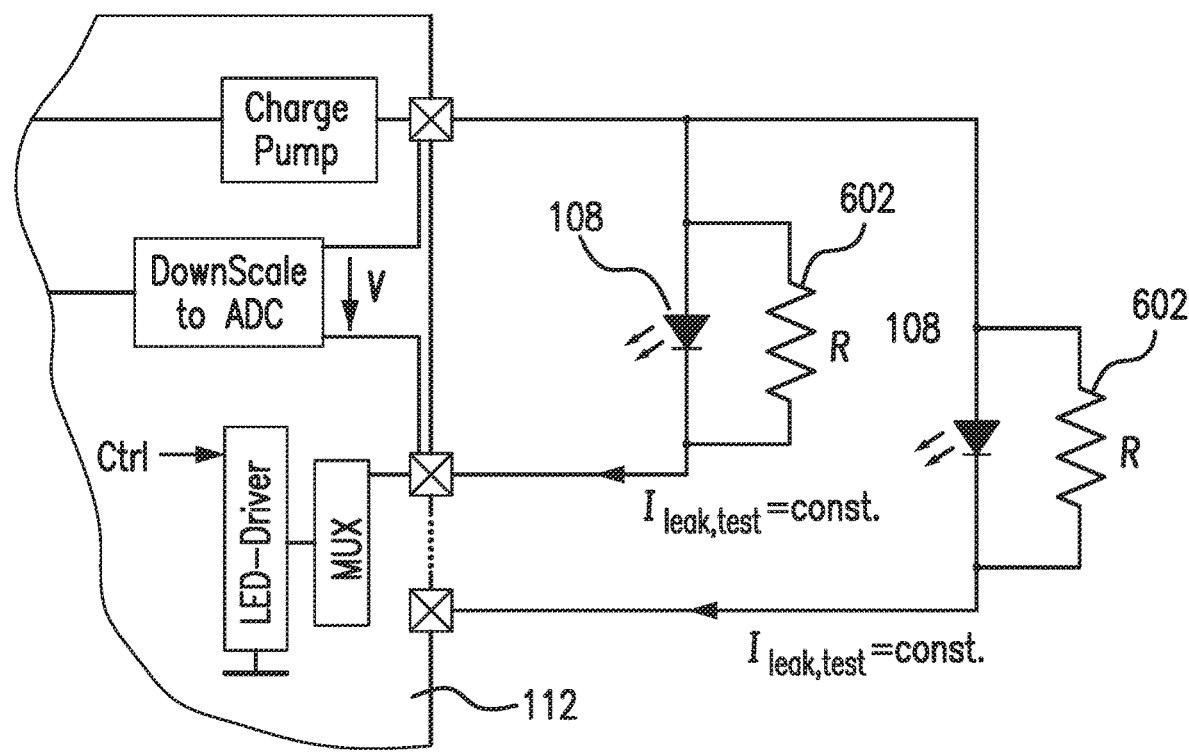
FIG. 6 is a schematic view illustrating a circuit for measuring light source impedance embodying aspects of the present invention.

In some embodiments, one or more of the sensing devices 100 may include one or more circuits for detecting the failure and/or degradation of one or more of the light sources 108. In some embodiments, the one or more circuits may detect the failure and/or degradation of one or more of the light sources 108 by measuring one or more characteristics of the one or more light sources 108. In some non-limiting embodiments, to detect a disconnection, the one or more circuits may measure the supply voltage across one or more of the light sources 108 while supplying a specified current to the one or more light sources 108. In some non-limiting embodiments, the one or more circuits may alternatively or additionally measure the impedance of one or more of the light sources 108. FIG. 6 is a schematic view illustrating a non-limiting example of a circuit for measuring light source impedance in an embodiment in which the light sources 108 are mounted on the substrate 112. As shown in FIG. 6, one or more of the light sources 108 of a sensing device 100 may include parasitic resistance 602 and circuitry to measure the voltage drop(s) across the one or more light sources 108. In some non-limiting embodiments, the circuitry to measure the voltage drop(s) may be fabricated in the substrate 112. The circuitry shown in FIG. 6 may allow the sensing device 100 to detect a parallel current path or "short circuiting" that results in lower or "noisy" light output from the one or more light sources 108. In some non-limiting embodiments, the one or more circuits may alternatively or additionally measure light output from the one or more light sources 108 with adjacent photodetectors 224, 226. In some embodiments, if the light measured by the photodetectors drops below a threshold, the analyte monitoring system 50 (e.g., the transceiver 101 of the analyte monitoring system 50) may determine that the output of the light source 108 is degraded.

In some embodiments, the one or more of the analyte indicator element 106, light source(s) 108, photodetectors 224, 226, circuit components 111, and substrate 112 of the sensing devices 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the system housing 104, sensing devices 100, and/or transceiver 101 may be as described in one or more of U.S. application Ser. Nos. 13/761,839, 13/937,871, 13/650,016, and 14/142,017. For instance, the system housing 104 may have one or more hydrophobic, hydrophilic, opaque, and/or immune response blocking membranes or layers on the exterior thereof.

Although in some embodiments, as illustrated in FIG. 2, the sensing devices 100 may be an optical sensing devices, this is not required, and, in one or more alternative embodiments, sensing devices 100 may be a different types of analyte sensing devices, such as, for example, diffusion sensing devices or pressure sensing devices. Also, although in some embodiments, as illustrated in FIG. 1, the multisite sensing system 105 may be a fully implantable sensing system, this is not required, and, in some alternative embodiments, the sensing system 105 may be a transcutaneous sensing system having a wired connection to the transceiver 101. For example, in some alternative embodiments, the sensing system 105 may be located in or on a transcutaneous needle (e.g., at the tip thereof). In these embodiments, instead of wirelessly communicating using inductive elements 103 and 114, the sensing system 105 and transceiver 101 may communicate using one or more wires connected between the transceiver 101 and the transceiver transcutaneous needle that includes the sensing system 105. For another example, in some alternative embodiments, the sensing system 105 may be located in a catheter (e.g., for intravenous blood glucose monitoring) and may communicate (wirelessly or using wires) with the transceiver 101.

In some embodiments, the sensing system 105 may include a transceiver interface device. In some embodiments, the transceiver interface device may include the antenna (e.g., inductive element 114) of the sensing system 105. In some of the transcutaneous embodiments where there exists a wired connection between the multisite sensing system 105 and the transceiver 101, the transceiver interface device may include the wired connection.

Figure 7:
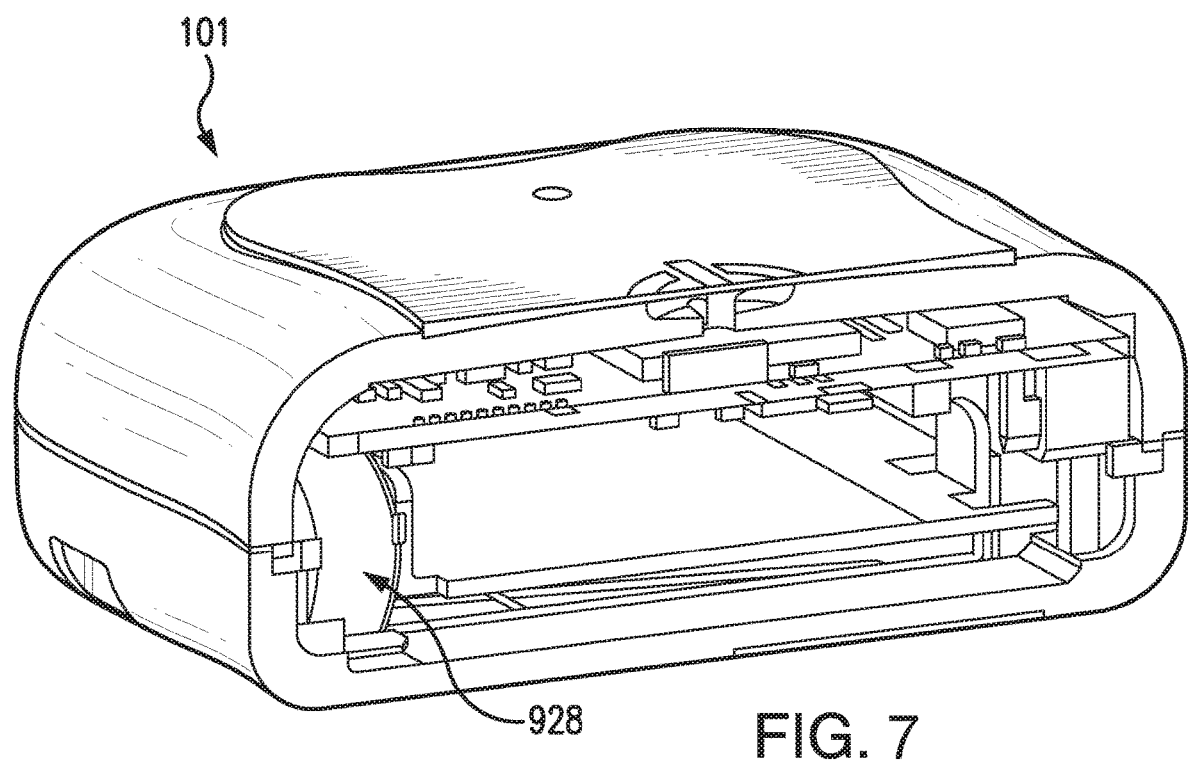
FIG. 7 is cross-sectional, perspective view of a transceiver embodying aspects of the invention.
Figure 8:
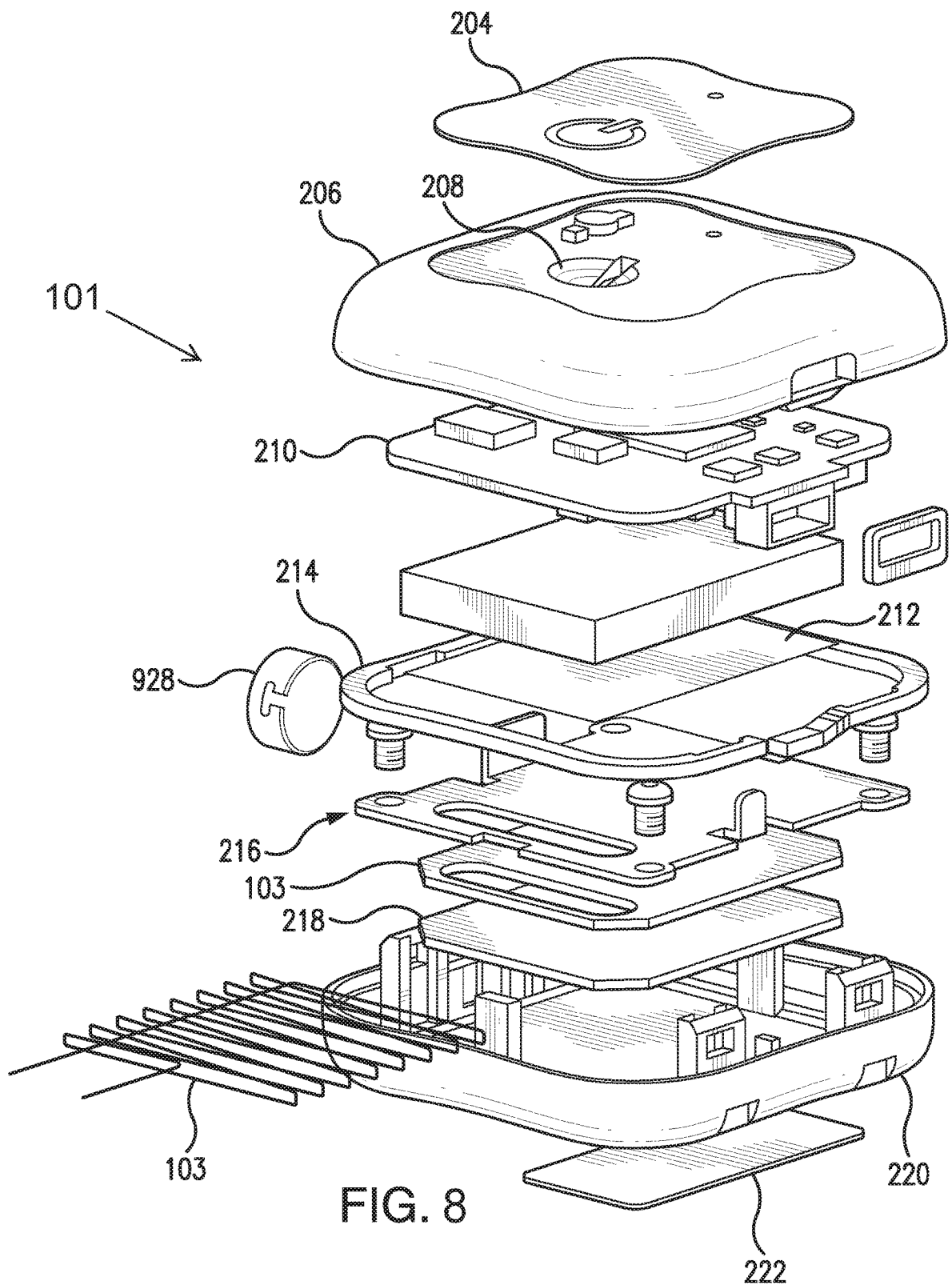
FIG. 8 is an exploded, perspective view of a transceiver embodying aspects of the invention.

FIGS. 7 and 8 are cross-sectional and exploded views, respectively, of a non-limiting embodiment of the transceiver 101, which may be included in the analyte monitoring system 50 illustrated in FIG. 1. As illustrated in FIG. 8, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 7 and 8, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 9:
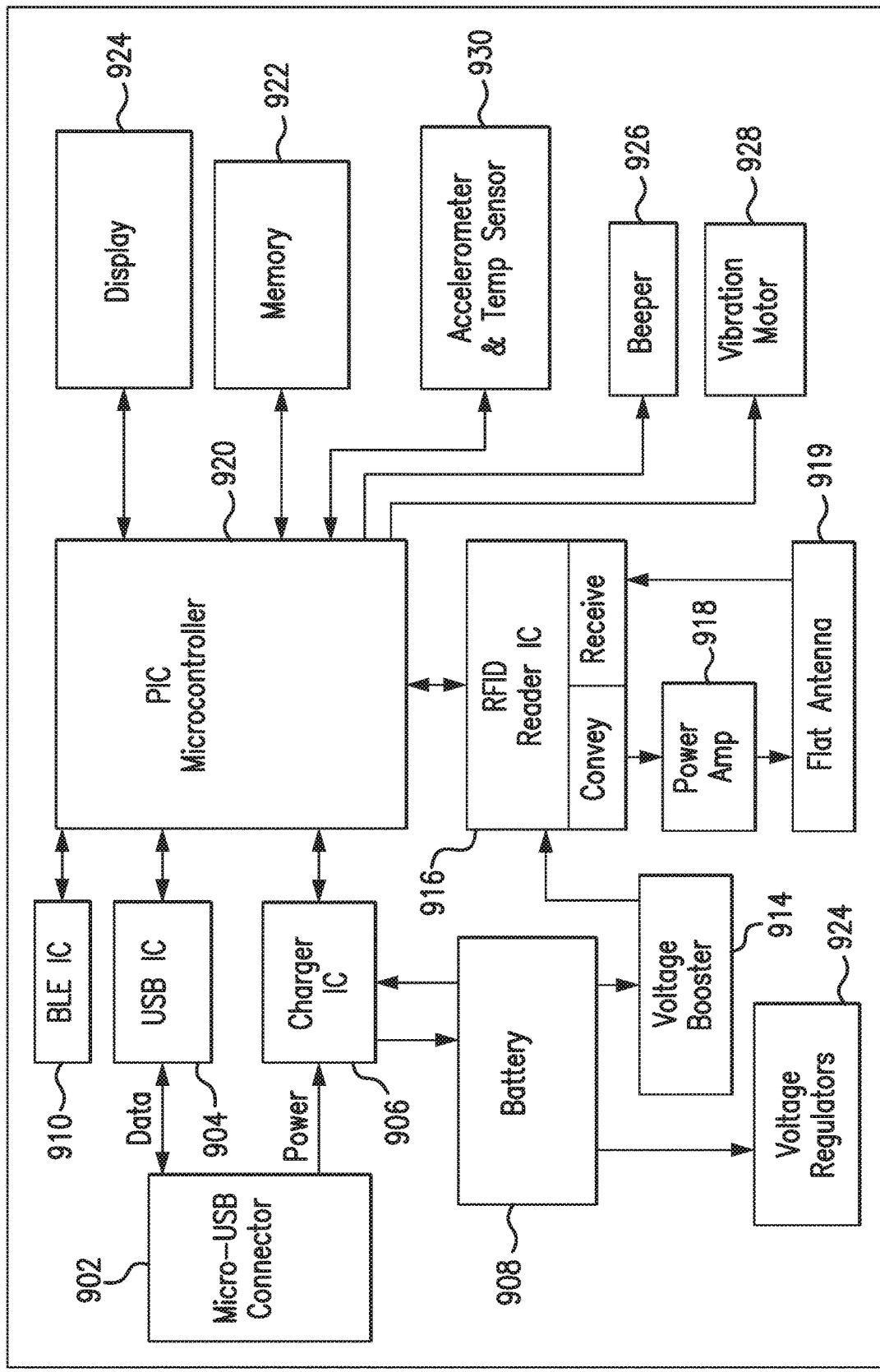
FIG. 9 is a schematic view illustrating a transceiver embodying aspects of the present invention.

FIG. 9 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 107 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 107 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 107 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 107. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

In some embodiments, the transceiver 101 may include a peripheral interface controller (PIC) controller 920 and memory 922 (e.g., Flash memory), which may be non-volatile and/or capable of being electronically erased and/or rewritten. The PIC controller 920 may control the overall operation of the transceiver 101. For example, the PIC controller 920 may control the connector IC 904 or wireless communication IC 910 to transmit data via wired or wireless communication and/or control the RFID reader IC 916 to convey data via the inductive element 103. The PIC controller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC controller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC controller 920.

In some embodiments, the sensing devices 100 of the sensing system 105 may each be radio frequency identification (RFID) devices. The sensing devices 100 may be powered by a radio frequency (RF) signal from the external transceiver 101, and the multiple sensing devices 100 may draw more energy than if only a single sensing device 100 were drawing energy.

For example, in some embodiments, all communication in the analyte monitoring system 50 between the transceiver 101 and the sensing devices 100 of the sensing system 105 may be accomplished through addressed commands. In these embodiments, as shown in the table below, in order to cause each of the N sensing devices 100 to perform a measurement sequence and convey measurement data, the transceiver 101 may convey an addressed measurement command to each of the N sensing devices 100 and then convey an addressed read command to each of the N sensing devices. That is, the transceiver 101 may convey 2N addressed commands to cause each of the sensing devices 100 to perform a measurement and sequence and convey measurement data. In some embodiments, the transceiver 101 may convey addressed commands (e.g., addressed measurement commands instead of the unaddressed measurement commands described in the paragraph below) in situations where there is not enough power for the sensing devices 100 to execute the commands in parallel. See, e.g., FIG. 15.

|  | Measure Device 1 | Measure Device 2 | ... | Measure Device N | Read Device 1 | Read Device 2 | ... | Read Device N |
|---|---|---|---|---|---|---|---|---|
| Device 1 | X |  |  |  | X |  |  |  |
| Device 2 |  | X |  |  |  | X |  |  |
| ... |  |  |  |  |  |  | ... |  |
| Device N |  |  |  | X |  |  |  | X |

In some alternative embodiments, the analyte monitoring system 50 may use non-addressed communication for some or all communication between the transceiver 101 and the sensing devices 100 of the sensing system 105 when one or more commands can be performed by the sensing devices 100 in parallel. In some embodiments, the analyte monitoring system 50 may maximize the number of unaddressed commands from the transceiver 101 to the sensing devices 100 of the sensing system 105 and minimize the number of addressed commands. In some embodiments, as shown in the table below, the transceiver 101 may convey an unaddressed measurement command, which causes the multiple sensing devices 100 of the sensing system 105 to perform measurement sequences in parallel, and then, to avoid collision, convey addressed read commands, which cause individual sensing devices 100 to convey measurement data. That is, by using an unaddressed measurement command, the transceiver 101 may convey N+1 commands to cause each of the sensing devices 100 to perform a measurement and sequence and convey measurement data. In this way, use of one or more unaddressed measurement commands may reduce the amount of energy used to get the multiple sensing devices 100 of the sensing system 105 to execute commands. As a result, the unaddressed measurement commands may help to minimize total communication time between the transceiver 101 and the sensing devices 100 of the sensing system 105, minimize energy expenditure by the transceiver 101, and/or maximize battery life in the transceiver 101.

|  | Unaddressed Measure | Read Device 1 | Read Device 2 | ... | Read Device N |
|---|---|---|---|---|---|
| Device 1 | X | X |  |  |  |
| Device 2 | X |  | X |  |  |
| ... | ... |  |  | ... |  |
| Device N | X |  |  |  | X |

Figure 10:
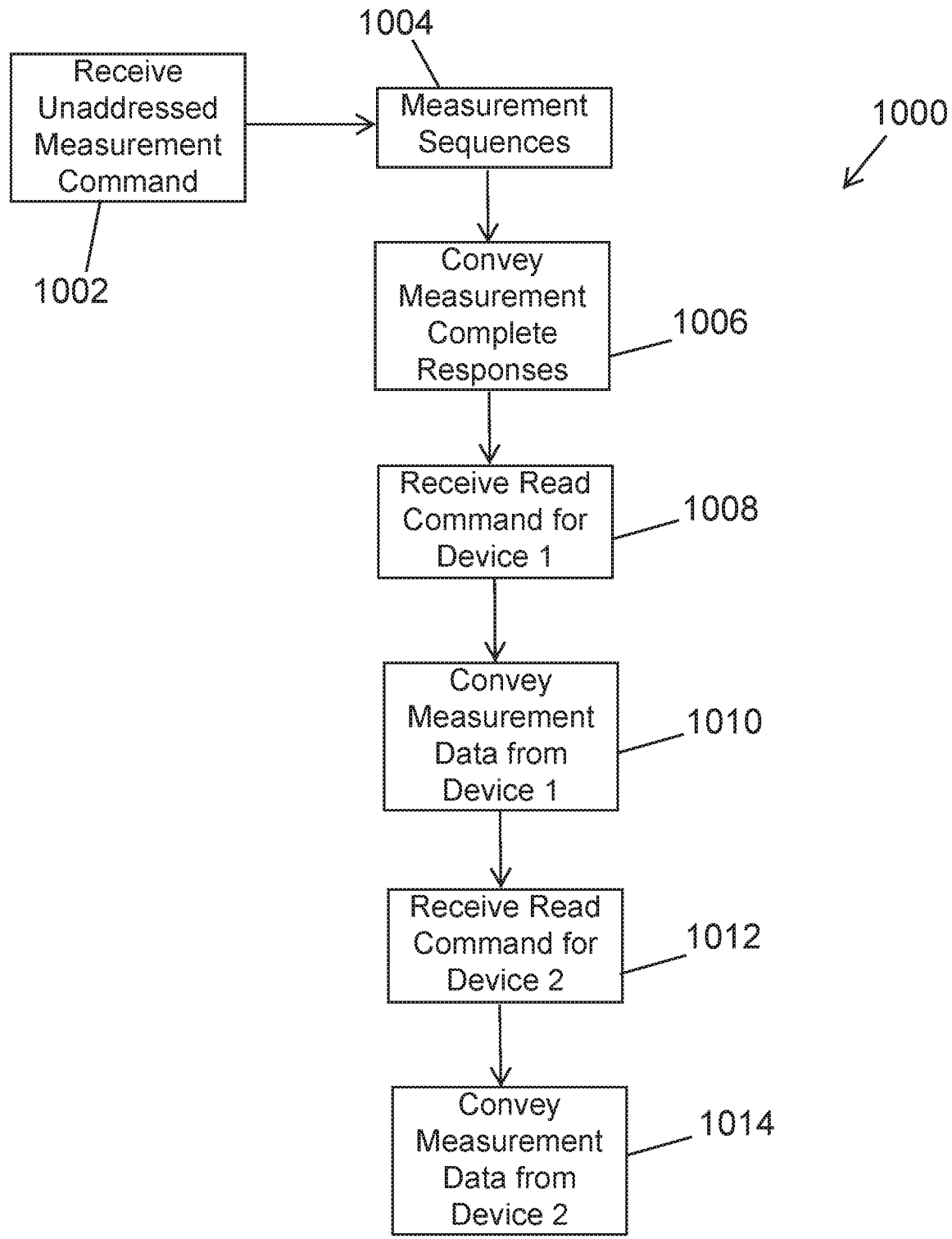
FIG. 10 is a flow chart illustrating a process for taking and conveying measurement data from multiple sensing devices in a sensing system embodying aspects of the present invention.

FIG. 10 illustrates non-limiting embodiment of a measurement and measurement data conveyance process 1000 that may be performed by a sensing system 105 having multiple sensing devices 100. The process 1000 may include a step 1002 of receiving an unaddressed measurement command from the transceiver 101. The process 1000 may include a step 1004 in which, in response to the received unaddressed measurement command, each of two or more sensing devices 100 of the sensing system 105 may perform a measurement sequence. In some embodiments, the measurement sequence may include one or more of (i) one or more analyte signal measurement (e.g., using one or more signal photodetectors 224) with one or more light sources 108 (e.g., ultraviolet light sources) on, (ii) one or more reference signal measurements (e.g., using one or more reference photodetectors 226) with one or more light sources 108 (e.g., ultraviolet light sources) on, (iii) one or more ambient light measurements (e.g., using one or more photodetectors 224 and/or 226) with no light source 108 on, (iv) one or more signal measurement (e.g., using one or more signal photodetectors 224) with one or more different light sources 108 (e.g., blue light sources) on, (v) one or more temperature measurements using one or more temperature transducers, and (vi) one or more light source impedance measurements. In some embodiments, the measurement sequence may include storing the measurement data in a memory or register of the sensing device 100.

Figure 12:
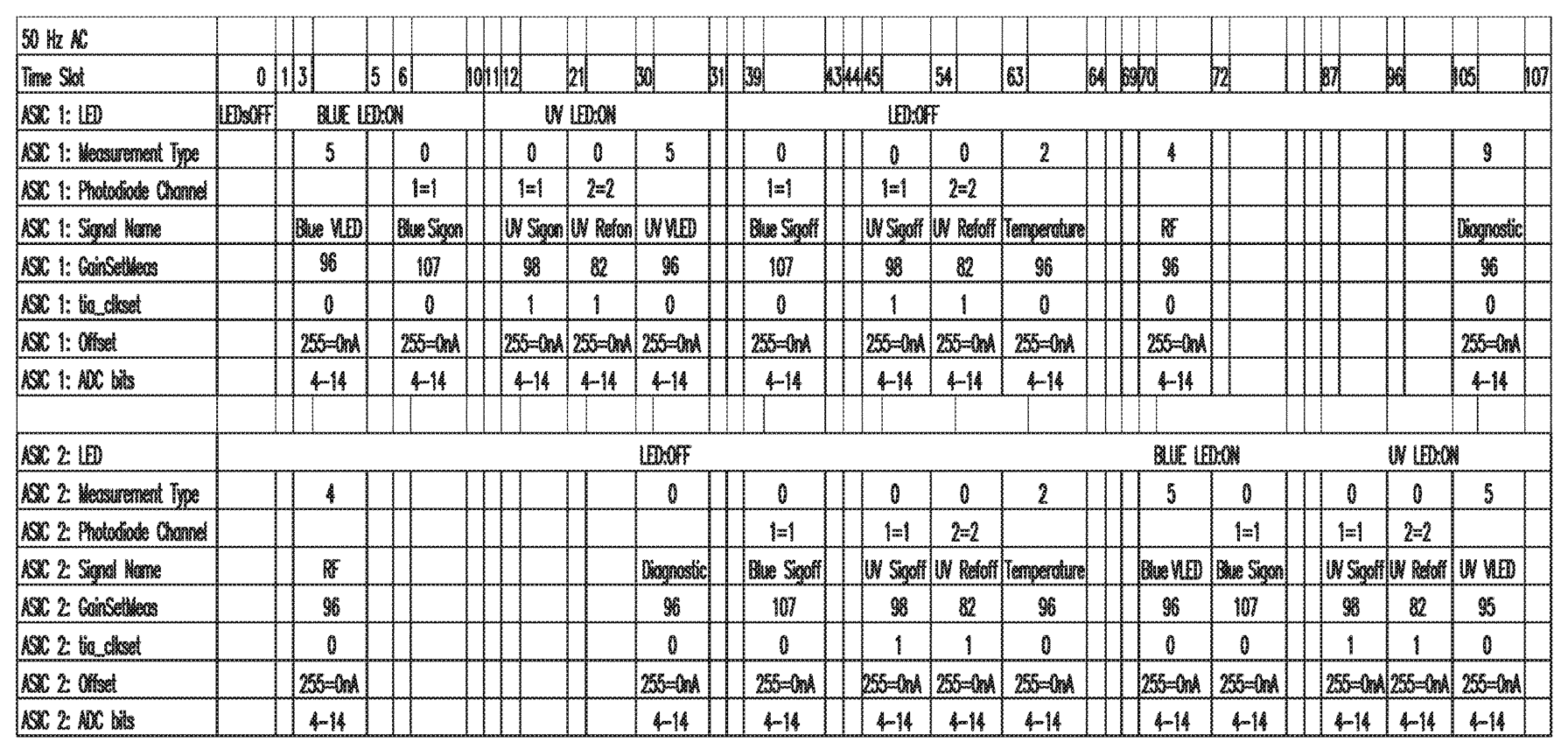

In some embodiments, one or more of the sensing devices 100 may perform the same measurement sequence. FIG. 11 illustrates a non-limiting example of the measurement sequences that may be performed by first and second sensing devices 100 of a sensing system 105 according to an embodiment where the first and second sensing devices 100 perform the same measurement sequence. However, two or more sensing devices 100 of a sensing system 105 performing the same measurement sequence at the same time may result in interference between one or more of the measurements. Accordingly, in some embodiments, one or more of the sensing devices 100 may be configured to have a programmable measurement cycle, and one or more of the sensing devices 100 may be programmed to perform different measurement sequences. In some embodiments, the different measurement sequences may enable the sensing devices 100 to perform measurement activities in parallel while avoid simultaneous performance of measurement activities that would result in interference. In some embodiments, the different measurement sequences may be configured such one sensing device 100 performs measurements at times that minimize interference with the measurements of another sensing device 100 and vice versa. In some non-limiting embodiments, the different measurement sequences of the sensing devices 100 may avoid optical interference by having no more than one sensing device 100 turns on a light source 108 at a given time. That is, in some non-limiting embodiments, the different measurement sequences may avoid more than one of sending devices 100 turning on a light source 108 at a given time. In some embodiments, preventing more than one sensing device 100 from having a light source 108 on at the same time may also avoid electrical interference caused by the sensing devices 100 drawing too much power simultaneously. FIG. 12 illustrates a non-limiting example of the measurement sequences that may be performed by first and second sensing devices 100 of a sensing system 105 according to an embodiment where the first and second sensing devices 100 perform the different measurement sequences, which do not interfere with each other.

In some embodiments, the process 1000 may include a step 1006 in which the sensing devices 100 convey a measurement complete response to the transceiver 101. In some embodiments, one or more of the measurement complete responses may collide. In some embodiments, to avoid collision, one or more of the sensing devices 100 may be configured to convey measurement complete responses at different times.

In some embodiments, the process 1000 may include a step 1008 in which the sensing system 105 receives an addressed read measurement data command. The addressed read measurement data command may be addressed to a first one of the sensing devices 100. In some embodiments, the process 1000 may include a step 1010 in which only the sensing device 100 to which the measurement data command is addressed responds to the addressed read measurement data command by conveying the measurement data to the transceiver 101.

In some embodiments, the process 1000 may include a step 1012 in which the sensing system 105 receives an addressed read measurement data command. The addressed read measurement data command may be addressed to a second one of the sensing devices 100. In some embodiments, the process 1000 may include a step 1014 in which only the sensing device 100 to which the measurement data command is addressed responds to the addressed read measurement data command by conveying the measurement data to the transceiver 101.

In embodiments where the sensing system 105 includes three or more sensing devices 100, the process 1000 may include additional receiving addressed read measurement data command steps and additional conveying measurement data steps so that the measurement data from all of the sensing devices 100 may be accessed.

Figure 13:
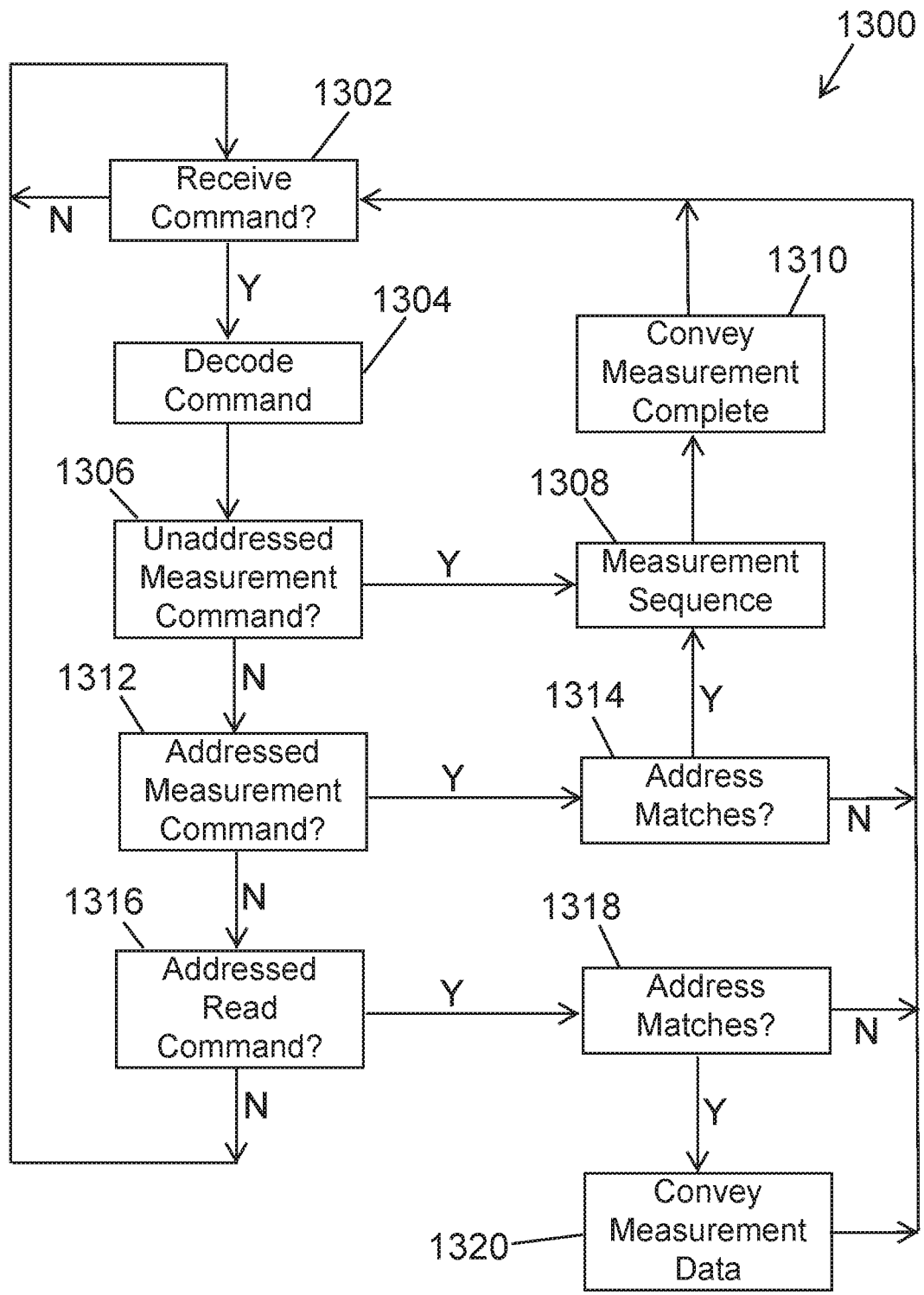
FIG. 13 is a flow chart illustrating a process for taking and conveying measurement data from a multiple sensing device in a sensing system embodying aspects of the present invention.

FIG. 13 illustrates a non-limiting embodiment of a command receipt and performance process 1300 that may be performed by a sensing device 100 of a sensing system 105 having multiple sensing devices 100. In some non-limiting embodiments, the process 1300 may be performed by a controller (e.g., ASIC) of the sensing device 100. The process 1300 may include a step 1302 of determining whether a command has been received from the transceiver 101 (via the inductive element 114 and shared communication device 109 of the sensing system 105). In some embodiments, the process 1300 may include a step 1304 in which the sensing device 100 decodes the received command.

In some embodiments, the process 1300 may include a step 1306 of determining whether the received command is an unaddressed measurement command. In some embodiments, if the sensing device 100 determines that the received command is an unaddressed measurement command, the process 1300 may proceed to a step 1308 in which the sensing device 100 performs a measurement sequence. In some embodiments, the process 1300 may include a step 1310 in which the sensing device 100 conveys a measurement complete response to the transceiver 101 (via the shared communication device 109 and inductive element 114 of the sensing system 105) after completing the measurement sequence.

In some embodiments, the process 1300 may include a step 1312 of determining whether the received command is an addressed measurement command. In some embodiments, if the sensing device 100 determines that the received command is an addressed measurement command, the process 1300 may proceed to a step 1314 in which the sensing device 100 determines whether the addressed measurement command is addressed to the sensing device 100. In some embodiments, the sensing device 100 may determine whether the addressed measurement command is addressed to the sensing device 100 by determining whether the address of the command matches the address of the sensing device 100. In some embodiments, if the address of the command matches the address of the sensing device 100, the process 1300 may proceed to steps 1308 and 1310 for performance of the measurement sequence and conveyance of a measurement complete response to the transceiver 101.

In some embodiments, the process 1300 may include a step 1316 of determining whether the received command is an addressed read measurement data command. In some embodiments, if the sensing device 100 determines that the received command is an addressed read measurement data command, the process 1300 may proceed to a step 1318 in which the sensing device 100 determines whether the addressed read measurement data command is addressed to the sensing device 100. In some embodiments, the sensing device 100 may determine whether the addressed read measurement data command is addressed to the sensing device 100 by determining whether the address of the command matches the address of the sensing device 100. In some embodiments, if the address of the command matches the address of the sensing device 100, the process 1300 may proceed to a step 1320 in which the sensing device 100 conveys stored measurement data to the transceiver 101 (via the shared communication device 109 and inductive element 114 of the sensing system 105).

In some embodiments, the multiple sensing devices 100 in the sensing system 105 may provide redundancy. For example, in some embodiments, the multiple sensing devices 100 may provide redundant electronic sensing systems (e.g., two or more sets of ASICs, light sources 108, photodetectors 224, 226, and optical filters). In some embodiments, the multiple sensing devices 100 may provide redundant chemical sensing systems (e.g., two or more analyte indicator elements 106 at different locations). In some non-limiting embodiments, the sensing system 105 may provide redundant sensing devices 100 with mesoscale separation (e.g., the analyte indicator elements 106 of the sensing device 100 may be in close enough proximity that they measure the same analyte concentration but be separated enough that distortion degradation mechanisms would affect each of the analyte indicator elements 106 differently).

In some embodiments, the transceiver 101 may detect degradation or distortion in one or more of the sensing devices 100 through the use of redundant systems. For instance, in some non-limiting embodiments, the transceiver 101 may determine whether the behavior of the two of the sensing devices 100 deviates from one another by more than a predetermine amount, and, if so, the transceiver 101 may determine that one of the sensing devices 100 (e.g., the analyte indicator element 106 and/or the electronic sensing system thereof) has been degraded or distorted.

In some embodiments, the transceiver 101 may improve measurement accuracy and/or reduce effective noise and distortion by weighting the measurement data received from each sensing device 100 (or weighting the analyte concentrations calculated from the measurement data). For instance, in some non-limiting embodiments, the transceiver 101 may determine the performance of the each of the sensing devices 100 and apply a weighting to the measurement data (or analyte concentration calculated therefrom) based on the performance of the sensing device 100 that produced the measurement data. In some non-limiting embodiments, the transceiver 101 may weight equally (i.e., average) the measurement data (or calculated analyte concentrations) when all of the sensing devices 100 of the sensing system 105 are performing equally well. In some non-limiting embodiments, the transceiver 101 may give less weight to measurement data (or calculated analyte concentrations) from a sensing device 100 that is performing at a lower level. In some non-limiting embodiments, the weight given to the measurement data (or calculated analyte concentration) may be proportional to the determined performance of the sensing device 100 that conveyed the measurement data. In some embodiments, the transceiver 101 remove or not give any weight to measurement data (or analyte concentrations) from sensing devices 100 that are considered to be sufficiently distorted or degraded.

In some embodiments, if the transceiver 101 detects that the performance of a sensing device 100 has dropped below a threshold (i.e., that degradation or distortion in a sensing device 100 has increased above a threshold, the transceiver 100 may isolate the sensing device 100. In some non-limiting embodiments, the transceiver 101 may isolate the sensing device 100 by not conveying read commands addressed to the sensing device 100. In some non-limiting embodiments, the transceiver 101 may send a turn-off command to a poorly performing sensing device 100, and, in response, the sensing device 100 may not perform measurement sequences in response to unaddressed measurement commands.

In some embodiments, the multiple sensing devices 100 of the sensing system 105 may extend the life of the sensing system 105 relative to a sensing system 105 having only a single sensing device 100. In some non-limiting embodiments, if a sensing device 100 in a sensing system 105 has reached the end of its life (e.g., because distortion or degradation of a sensing device 100 has caused the performance of the sensing device 100 to drop below a threshold level), the transceiver 101 may continue to use measurement data from one or more sensing devices 100 in the sensing system 105 that has not reached its end of life. In some non-limiting embodiments, all of the sensing devices 100 of a sensing system 105 may be used initially and then the number of sensing devices 100 used may be reduced as individual sensing devices 100 the end of their useful lives. In some alternative embodiments, one sensing device 100 (or a subset of sensing devices 100) may be used initially and then a different one (or a different subset of sensing devices 100) may be used when the initial one (or subset) reaches its end of useful life. In this way, the useful life of a sensing system 105 having N sensing devices 100 may be increased by N when compared to the useful life of a sensing system 105 having only a single sensing device 100.

Figure 14:
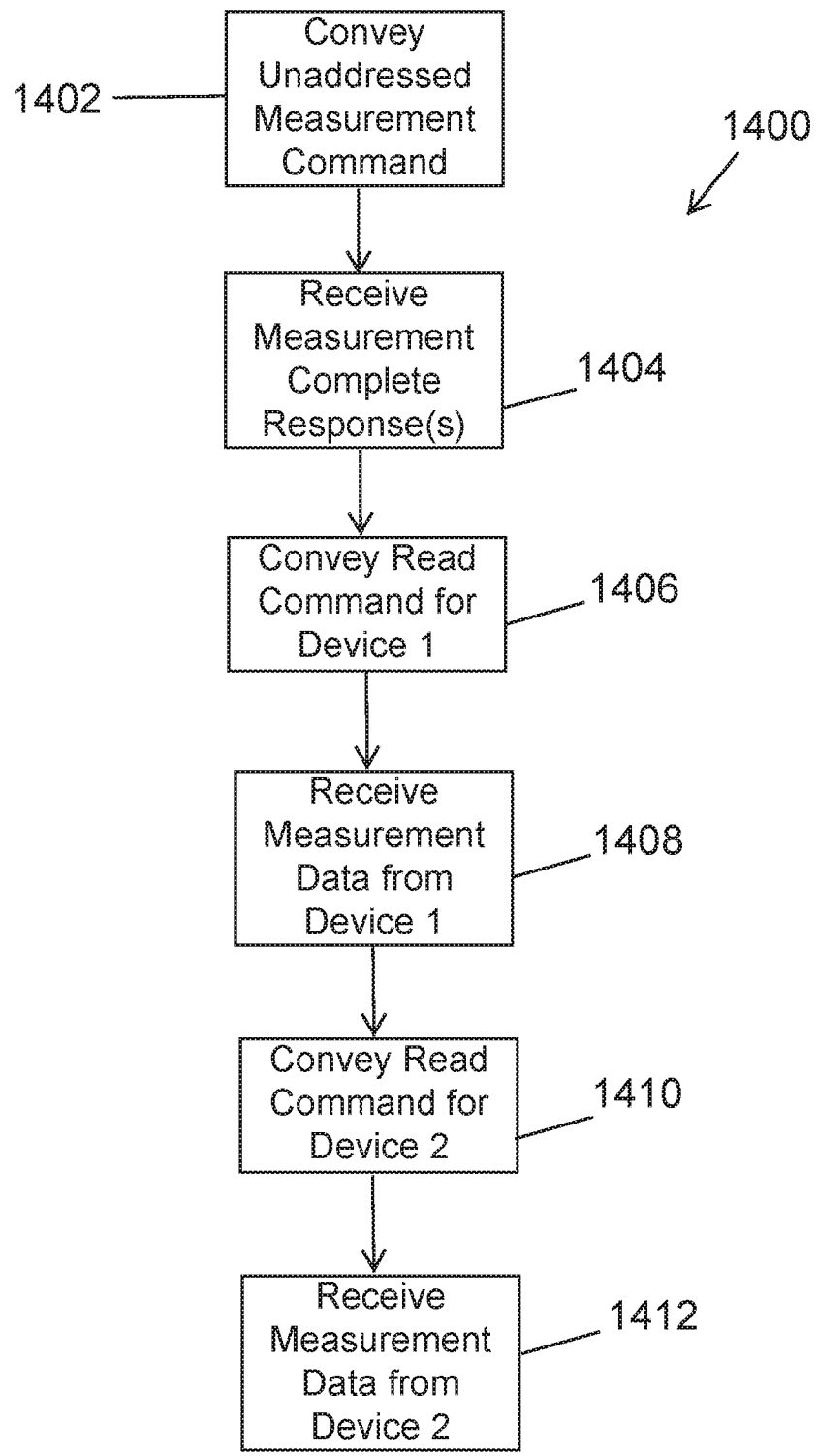
FIG. 14 is a flow chart illustrating a process for conveying measurement and read commands from a transceiver to multiple sensing devices of a sensing system embodying aspects of the present invention.

FIG. 14 illustrates a non-limiting embodiment of a measurement and read command conveyance process 1400 that may be performed by a transceiver 101 of an analyte monitoring system 50 that includes a sensing system 105 having multiple sensing devices 100. In some non-limiting embodiments, the PIC controller 920 of the transceiver 101 may be configured to perform one or more steps of the process 1400. In some embodiments, the process 1400 may include a step 1402 in which the transceiver 101 conveys an unaddressed measurement command to the sensing system 105. In some embodiments, the sensing devices 100 of the sensing system 105 may receive the unaddressed measurement command (e.g., via the inductive element 114 and shared communication device 109 of the sensing system 105), and the sensing devices 100 may perform a measurement sequence in response to the unaddressed measurement command and store measurement data obtained therefrom in a register or memory of the sensing device 100. In some non-limiting embodiments, one or more of the sensing devices 100 may have previously received a turn-off command from the transceiver 101 (e.g., due to poor performance), and those sensing devices 100 may not perform a measurement sequence in response to the unaddressed measurement command. In some embodiments, the process 1400 may include a step 1404 in which the transceiver 101 receives a measurement complete response from one or more of the sensing devices 100.

In some embodiments, the process 1400 may include a step 1406 in which the transceiver 101 conveys an addressed read measurement data command to the sensing system 105. The addressed read measurement data command may be addressed to a first one of the sensing devices 100. In some embodiments, the process 1400 may include a step 1408 in which the transceiver 101 receives measurement data from only the sensing device 100 to which the measurement data command is addressed.

In some embodiments, the process 1400 may include a step 1410 in which the transceiver 101 conveys an addressed read measurement data command to the sensing system 105. The addressed read measurement data command may be addressed to a second one of the sensing devices 100. In some embodiments, the process 1400 may include a step 1412 in which the transceiver 101 receives measurement data from only the sensing device 100 to which the measurement data command is addressed.

In embodiments where the sensing system 105 includes three or more sensing devices 100, the process 1400 may include additional conveying addressed read measurement data command steps and additional receiving measurement data steps so that transceiver 101 may access the measurement data from all of the sensing devices 100. In some non-limiting embodiments, the transceiver 101 may determine the performance of one or more of the sensing devices 100, and the transceiver 101 may only convey addressed read commands to sensing devices 100 of the sensing system 105 whose determined performance is above a threshold.

Figure 15:
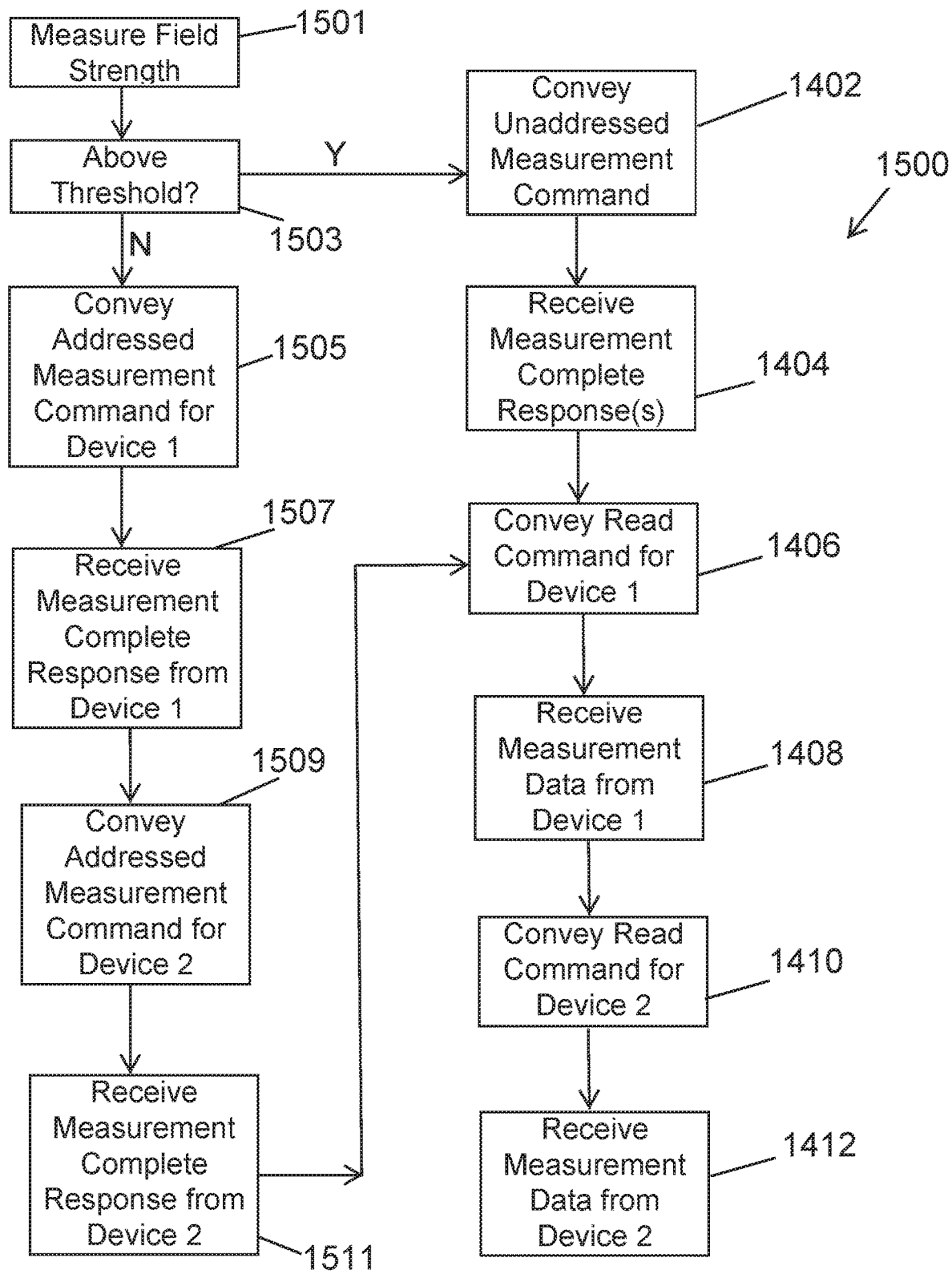
FIG. 15 is a process for conveying measurement and read commands from a transceiver to multiple sensing devices of a sensing system embodying aspects of the present invention.

FIG. 15 illustrates a non-limiting alternative embodiment of a measurement and read command conveyance process 1500 that may be performed by a transceiver 101 of an analyte monitoring system 50 that includes a sensing system 105 having multiple sensing devices 100. In some non-limiting embodiments, the PIC controller 920 of the transceiver 101 may be configured to perform one or more steps of the process 1500. In some embodiments, the process 1500 may include a step 1501 in which the transceiver 101 measures the field strength (e.g., the strength of coupling of the inductive element 103 of the transceiver 101 and the inductive element 114 of the sensing system 105 within an electrodynamic field). In some embodiments, the process 1500 may include a step 1503 in which the transceiver 101 compares the measured field strength to a threshold. In some embodiments, if the measured field strength is above the threshold (i.e., if the field strength is strong), the process 1500 may proceed to the unaddressed measurement command conveyance step 1402, the measurement complete response receiving step 1404, the first sensing device addressed read measurement data command conveyance step 1406, the first sensing device measurement data receiving step 1408, the second sensing device addressed read measurement data command conveyance step 1410, and the second sensing device measurement data receiving step 1412 described above with reference to FIG. 14.

In some embodiments, if the measured field strength is not above the threshold (i.e., if the field strength is weak), the process 1500 may from the field strength threshold comparison step 1503 to a step 1505 in which the transceiver 101 conveys an addressed measurement command to the sensing system 105. The addressed measurement command may be addressed to a first one of the sensing devices 100. In some embodiments, the sensing devices 100 of the sensing system 105 may receive the addressed measurement command (e.g., via the inductive element 114 and shared communication device 109 of the sensing system 105), and the sensing device 100 to which the measurement command is addressed may perform a measurement sequence in response to the addressed measurement command and store measurement data obtained therefrom in a register or memory of the sensing device 100. In some embodiments, the process 1500 may include a step 1507 in which the transceiver 101 receives a measurement complete response from the sensing device 100 to which the addressed measurement command was addressed.

In some embodiments, the process 1500 may include a step 1509 in which the transceiver 101 conveys an addressed measurement command to the sensing system 105. The addressed measurement command may be addressed to a second one of the sensing devices 100. In some embodiments, the sensing devices 100 of the sensing system 105 may receive the addressed measurement command (e.g., via the inductive element 114 and shared communication device 109 of the sensing system 105), and the sensing device 100 to which the measurement command is addressed may perform a measurement sequence in response to the addressed measurement command and store measurement data obtained therefrom in a register or memory of the sensing device 100. In some embodiments, the process 1500 may include a step 1511 in which the transceiver 101 receives a measurement complete response from the sensing device 100 to which the addressed measurement command was addressed.

In some embodiments, the process 1500 may proceed from the second sensing device measurement complete response receiving step 1511 to the first sensing device addressed read measurement data command conveyance step 1406, the first sensing device measurement data receiving step 1408, the second sensing device addressed read measurement data command conveyance step 1410, and the second sensing device measurement data receiving step 1412 described above with reference to FIG. 14.

In some embodiments where the sensing system 105 includes three or more sensing devices 100, the process 1500 may include additional addressed measurement command conveyance steps and additional measurement complete response receiving steps so that the transceiver 101 may cause all of the sensing devices 100. In some non-limiting embodiments, the transceiver 101 may determine the performance of one or more of the sensing devices 100, and the transceiver 101 may only convey addressed measurement commands to sensing devices 100 of the sensing system 105 whose determined performance is above a threshold.

In some embodiments where the sensing system 105 includes three or more sensing devices 100, the process 1500 may include additional conveying addressed read measurement data command steps and additional receiving measurement data steps so that transceiver 101 may access the measurement data from all of the sensing devices 100. In some non-limiting embodiments, the transceiver 101 may determine the performance of one or more of the sensing devices 100, and the transceiver 101 may only convey addressed read commands to sensing devices 100 of the sensing system 105 whose determined performance is above a threshold.

Figure 16:
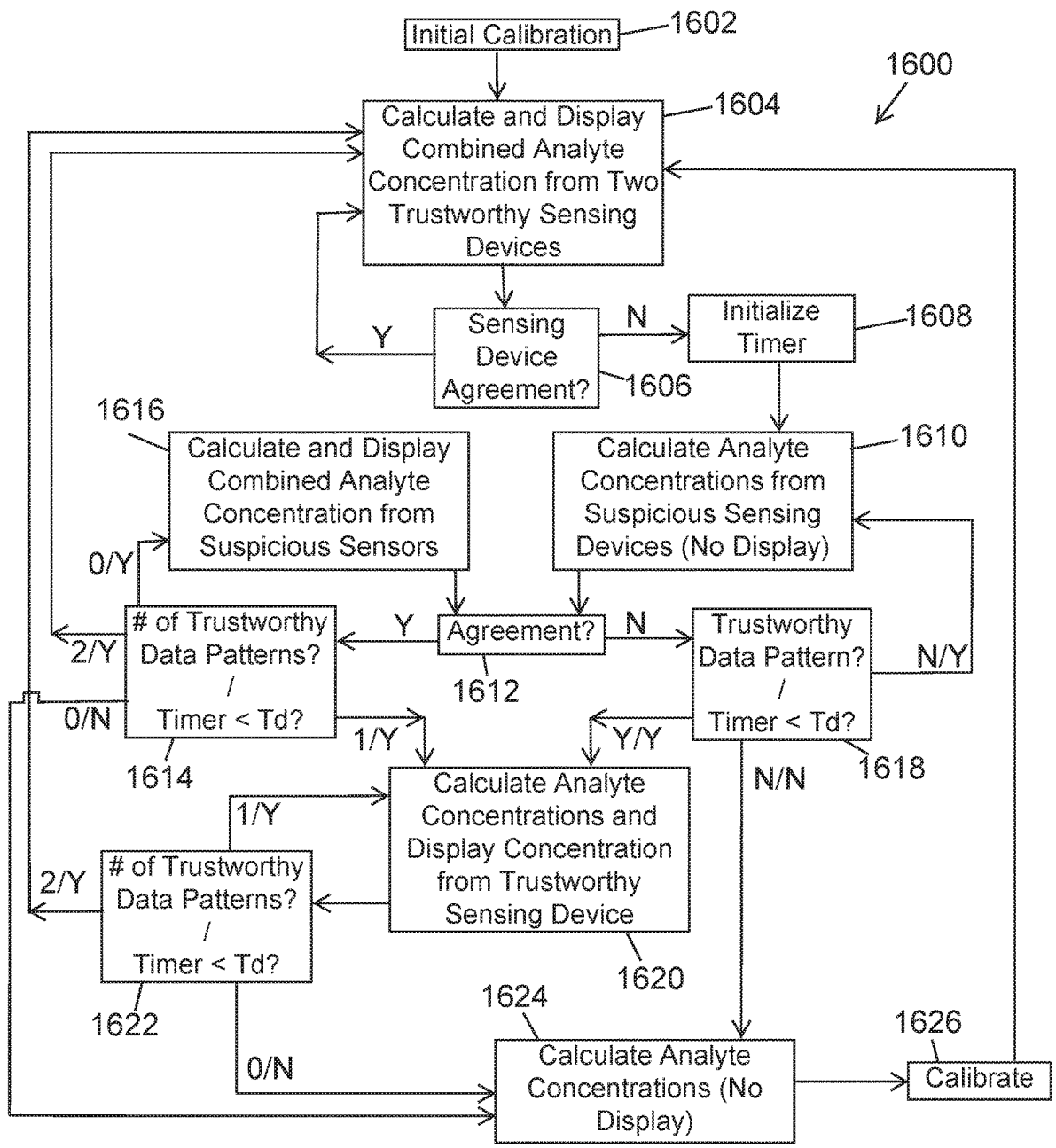
FIG. 16 is a process for calculating and displaying analyte concentrations using measurement data from multiple sensing devices of a sensing system embodying aspects of the present invention.

FIG. 16 illustrates a non-limiting embodiment of an analyte concentration calculation and display process 1600 that may be performed by a transceiver 101 of an analyte monitoring system 50 that includes a sensing system 105 having two sensing devices 100. Although the illustrated embodiment is for an analyte monitoring system 50 that includes a sensing system 105 having two sensing devices 101, this is not required, and, in some alternative embodiments, the analyte concentration calculation and display process 1600 may be applied to analyte monitoring system 50 that includes a sensing system 105 having more than two sensing devices 101 (e.g., three, four, six, eight sensing devices 101 etc.). In some non-limiting embodiments, the PIC controller 920 of the transceiver 101 may be configured to perform one or more steps of the process 1600.

In some embodiments, the process 1600 may include a step 1602 in which the transceiver 101 performs an initial calibration of the sensing devices 100 of the sensing system 105. In some non-limiting embodiments, the initial calibration of the sensing devices 100 may include prompting the user for calibration information. In some non-limiting embodiments, the transceiver 101 may prompt the user for calibration information by causing the display device 107 to display an indication that calibration information is needed. In some embodiments, the transceiver 101 may prompt the user for calibration information until calibration information is received. In some non-limiting embodiments, the user may enter calibration information into the display device 107, and the transceiver 101 may receive the calibration information from the display device 107. However, this is not required, and, in some alternative embodiments, the transceiver 101 may receive the calibration information in other ways (e.g., the user may enter the calibration information directly into the transceiver 101). In some non-limiting embodiments, the calibration information may be an analyte measurement using a blood sample (e.g., a finger stick measurement) such as, for example and without limitation, a self-monitoring blood glucose (SMBG) measurement. In some non-limiting embodiments, during the initial calibration, the transceiver 101 may prompt the user for multiple analyte measurements over a period of time. In some embodiments, the transceiver 101 may calibrate the sensing devices 100 of the sensing system 105 using the received calibration information.

In some embodiments, the initial calibration may include initializing weightings used to calculate combined analyte concentrations. In some embodiments, the weightings may be applied to analyte concentrations calculated using measurement information from individual sensing devices 100. In some non-limiting embodiments, the weightings may be initialized to the same value (e.g., 1 or 0.5) so that the analyte concentration calculated for each sensing device 100 may be weighted equally. In some non-limiting embodiments, the equal weighting may result in the combined analyte concentration being the average of the analyte concentrations from each sensing device 100. In some non-limiting embodiments, weightings may be dynamic PARD weightings (i.e., DPARD weightings).

In some embodiments, the process 1600 may include a step 1604 in which both sensing devices 100 of the sensing system 105 are considered trustworthy. In some embodiments, in step 1604, the transceiver 101 may perform a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some embodiments, in step 1604, the transceiver 101 may use the measurement data received from each sensing device 100 to calculate an analyte concentration for each sensing device 100 individually. In some embodiments, in step 1604, the transceiver 101 may calculate a combined analyte concentration using the individual analyte concentrations. In some non-limiting embodiments, the combined analyte concentration may be, for example and without limitation, a weighted average of the individual analyte concentrations. In some non-limiting embodiments, the weightings may be DPARD weightings. In some embodiments, in step 1604, the transceiver 101 may display the combined analyte concentration. In some non-limiting embodiments, the transceiver 101 may display the combined analyte concentration by conveying the combined analyte concentration to the display device 107 for display on a user interface. In some embodiments, the process 1600 may proceed from step 1604 to a step 1606.

In some embodiments, the process 1600 may include a step 1606 in which the transceiver 101 determines whether the individual analyte concentrations calculated in step 1604 using measurement data received from the sensing devices 100 are in agreement. In some non-limiting embodiments, the transceiver 101 may determine that the sensing devices 100 are in agreement if the individual analyte concentrations are within an agreement threshold. In some non-limiting embodiments, the agreement threshold may be a set amount (e.g., ±2 mg/dL or ±0.1 mmol/L) or a percent difference (e.g., ±5%). If the individual analyte concentrations are within the agreement threshold, the process 1600 may proceed back to step 1604. If the individual analyte concentrations are outside the agreement threshold, the process 1600 may proceed to a step 1608.

In some embodiments, the process 1600 may include a step 1608 in which the transceiver 101 initializes a disagreement timer. In some non-limiting embodiments, the transceiver 101 may initialize a disagreement timer to zero. In some embodiments, the disagreement timer may keep track of how long the individual analyte concentrations of the sensing devices 100 of the sensing system 105 have been in disagreement. In some embodiments, the process 1600 may proceed from step 1608 to a step 1610.

In some embodiments, the process 1600 may include a step 1610 in which the transceiver 101 considers both sensing devices 100 of the sensing system 105 suspicious and blinds the analyte monitoring system 50. In some embodiments, in step 1610, the transceiver 101 may perform a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some embodiments, in step 1610, the transceiver 101 may use the measurement data received from each sensing device 100 to calculate an analyte concentration for each sensing device 100 individually. In some embodiments, in step 1610, the transceiver 101 may calculate a combined analyte concentration using the individual analyte concentrations. In some non-limiting embodiments, the combined analyte concentration may be, for example and without limitation, a weighted average of the individual analyte concentrations. In some non-limiting embodiments, the weightings may be DPARD weightings. However, a combined analyte concentration in step 1610 is not required, and, in some alternative embodiments, in step 1610, the transceiver 101 may not calculate a combined analyte concentration. In some embodiments, in step 1610, the transceiver 101 may blind the analyte monitoring system 50. That is, in some embodiments, the transceiver 101 may cause the analyte monitoring system 50 to not display any of the combined analyte concentration and the individual analyte concentrations. In some non-limiting embodiments, the transceiver 101 may not convey any of the combined analyte concentration and the individual analyte concentrations to the display device 107 for display. In some embodiments, the process 1600 may proceed from step 1610 to a step 1612 to determine whether the individual analyte concentrations are in agreement.

In some embodiments, the process 1600 may include a step 1612 in which the transceiver 101 determines whether the individual analyte concentrations calculated in step 1610 (or in step 1616) using measurement data received from the sensing devices 100 are in agreement. In some non-limiting embodiments, the transceiver 101 may determine that the sensing devices 100 are in agreement if the individual analyte concentrations are within an agreement threshold. In some non-limiting embodiments, the agreement threshold may be a set amount (e.g., ±2 mg/dL or ±0.1 mmol/L) or a percent difference (e.g., ±5%). If the individual analyte concentrations are within the agreement threshold, the process 1600 may proceed back to a step 1614. If the individual analyte concentrations are outside the agreement threshold, the process 1600 may proceed to a step 1618.

In some embodiments, the process 1600 may include a step 1614 in which the transceiver 101 determines the number of trustworthy sensing device data patterns. In some embodiments, the transceiver 101 may analyze the current individual analyte concentration and one or more previous individual analyte concentrations from a sensing device 100 to determine whether the data pattern from the sensing device 100 is trustworthy. In some embodiments, in step 1614, the transceiver 101 may additionally determine whether the disagreement timer is less than a disagreement timer threshold Td. In some embodiments, if the transceiver 101 determines that the data patterns from both sensing devices 100 of the sensing system 105 are trustworthy, the process 1600 may proceed to step 1604 in which both sensing devices 100 are considered trustworthy. In some non-limiting embodiments, if in step 1618 the transceiver 101 determines that the data patterns from both sensing devices 100 are trustworthy, the process 1600 may proceed to step 1604 regardless of whether the disagreement timer is less than the disagreement timer threshold Td. In some embodiments, if in step 1618 the transceiver 101 determines that the data pattern from only one of the sensing devices 100 of the sensing system 105 is trustworthy and that the disagreement timer is less than the disagreement timer threshold Td, the process 1600 may proceed to a step 1620 in which only one sensing device 100 is considered trustworthy. In some embodiments, if in step 1618 the transceiver 101 does not determine that any of the data patterns from the sensing devices 100 of the sensing system 105 is trustworthy and determines that the disagreement timer is less than the disagreement timer threshold Td, the process 1600 may proceed to a step 1616. In some embodiments, if in step 1618 the transceiver 101 does not determine that any of the data patterns from the sensing devices 100 of the sensing system 105 are trustworthy and determines that the disagreement timer is not less than the disagreement timer threshold Td, the process 1600 may proceed to a step 1624.

In some embodiments, the process 1600 may include a step 1616 in which the transceiver 101 considers both sensing devices 100 of the sensing system 105 suspicious but, because the sensing devices 100 are in agreement, displays a combined analyte concentration. In some embodiments, in step 1616, the transceiver 101 may perform a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some embodiments, in step 1616, the transceiver 101 may use the measurement data received from each sensing device 100 to calculate an analyte concentration for each sensing device 100 individually. In some embodiments, in step 1616, the transceiver 101 may calculate a combined analyte concentration using the individual analyte concentrations. In some non-limiting embodiments, the combined analyte concentration may be, for example and without limitation, a weighted average of the individual analyte concentrations. In some non-limiting embodiments, the weightings may be DPARD weightings. In some embodiments, in step 1616, the transceiver 101 may display the combined analyte concentration. In some non-limiting embodiments, the transceiver 101 may display the combined analyte concentration by conveying the combined analyte concentration to the display device 107 for display on a user interface. In some embodiments, the process 1600 may proceed from step 1616 to step 1612 to determine whether the individual analyte concentrations are in agreement.

In some embodiments, the process 1600 may include a step 1618 in which the transceiver 101 determines whether a sensing device data pattern is trustworthy. In some embodiments, the transceiver 101 may analyze the current individual analyte concentration and one or more previous individual analyte concentrations from a sensing device 100 to determine whether the data pattern from the sensing device 100 is trustworthy. In some embodiments, in step 1618, the transceiver 101 may additionally determine whether the disagreement timer is less than a disagreement timer threshold Td. In some embodiments, if in step 1618 the transceiver 101 determines that the data pattern from a sensing device 100 of the sensing system 105 is trustworthy and that the disagreement timer is less than the disagreement timer threshold Td, the process 1600 may proceed to step 1620 in which only one sensing device 100 is considered trustworthy. In some embodiments, if in step 1618 the transceiver 101 does not determine that any of the data patterns from the sensing devices 100 of the sensing system 105 is trustworthy and determines that the disagreement timer is less than the disagreement timer threshold Td, the process 1600 may proceed to a step 1610. In some embodiments, if in step 1618 the transceiver 101 does not determine that any of the data patterns from the sensing devices 100 of the sensing system 105 are trustworthy and determines that the disagreement timer is not less than the disagreement timer threshold Td, the process 1600 may proceed to a step 1624.

In some embodiments, the process 1600 may include a step 1620 in which the transceiver 101 considers one sensing device 100 of the sensing system 105 trustworthy and the other sensing device 100 of the sensing system 105 suspicious, and the transceiver 101 displays the transceiver 101 displays an individual analyte concentration from the trustworthy sensing device 100. In some embodiments, in step 1620, the transceiver 101 may perform a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some embodiments, in step 1620, the transceiver 101 may use the measurement data received from each sensing device 100 to calculate an analyte concentration for each sensing device 100 individually. In some non-limiting embodiments, in step 1620, the transceiver 101 may calculate a combined analyte concentration using the individual analyte concentrations. However, this is not required and, in some alternative embodiments, in step 1620, the transceiver 101 may not calculate a combined analyte concentration. In some embodiments, in step 1620, the transceiver 101 may display the individual analyte concentration from the trustworthy sensing device 105. In some non-limiting embodiments, the transceiver 101 may display the combined analyte concentration by conveying the combined analyte concentration to the display device 107 for display on a user interface. In some embodiments, the process 1600 may proceed from step 1616 to step 1612 to determine whether the individual analyte concentrations are in agreement.

In some embodiments, the process 1600 may include a step 1622 in which the transceiver 101 in which the transceiver 101 determines the number of trustworthy sensing device data patterns. In some embodiments, the transceiver 101 may analyze the current individual analyte concentration and one or more previous individual analyte concentrations from a sensing device 100 to determine whether the data pattern from the sensing device 100 is trustworthy. In some embodiments, in step 1622, the transceiver 101 may additionally determine whether the disagreement timer is less than a disagreement timer threshold Td. In some embodiments, if the transceiver 101 determines that the data patterns from both sensing devices 100 of the sensing system 105 are trustworthy, the process 1600 may proceed to step 1604 in which both sensing devices 100 are considered trustworthy. In some non-limiting embodiments, if in step 1618 the transceiver 101 determines that the data patterns from both sensing devices 100 are trustworthy, the process 1600 may proceed to step 1604 regardless of whether the disagreement timer is less than the disagreement timer threshold Td. In some embodiments, if in step 1618 the transceiver 101 determines that the data pattern from only one of the sensing devices 100 of the sensing system 105 is trustworthy and that the disagreement timer is less than the disagreement timer threshold Td, the process 1600 may proceed to step 1620 in which only one sensing device 100 is considered trustworthy. In some embodiments, if in step 1618 the transceiver 101 does not determine that any of the data patterns from the sensing devices 100 of the sensing system 105 are trustworthy and determines that the disagreement timer is not less than the disagreement timer threshold Td, the process 1600 may proceed to step 1624.

In some embodiments, the process 1600 may include a step 1624 in which there are no trustworthy sensing devices 100 and blinds the analyte monitoring system 50. In some embodiments, in step 1624, the transceiver 101 may perform a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some embodiments, in step 1624, the transceiver 101 may use the measurement data received from each sensing device 100 to calculate an analyte concentration for each sensing device 100 individually. In some embodiments, in step 1624, the transceiver 101 may calculate a combined analyte concentration using the individual analyte concentrations. In some non-limiting embodiments, the combined analyte concentration may be, for example and without limitation, a weighted average of the individual analyte concentrations. In some non-limiting embodiments, the weightings may be DPARD weightings. However, a combined analyte concentration in step 1624 is not required, and, in some alternative embodiments, in step 1624, the transceiver 101 may not calculate a combined analyte concentration. In some embodiments, in step 1624, the transceiver 101 may blind the analyte monitoring system 50. That is, in some embodiments, the transceiver 101 may cause the analyte monitoring system 50 to not display any of the combined analyte concentration and the individual analyte concentrations. In some non-limiting embodiments, the transceiver 101 may not convey any of the combined analyte concentration and the individual analyte concentrations to the display device 107 for display. In some embodiments, the process 1600 may proceed from step 1624 to a step 1626 to recalibrate the sensing devices 100 of the sensing system 105.

In some embodiments, the process 1600 may include a step 1626 in which the transceiver 101 in which the transceiver 101 performs a calibration of the sensing devices 100 of the sensing system 105. In some non-limiting embodiments, the calibration of the sensing devices 100 may include prompting the user for calibration information. In some non-limiting embodiments, the transceiver 101 may prompt the user for calibration information by causing the display device 107 to display an indication that calibration information is needed. In some embodiments, the transceiver 101 may prompt the user for calibration information until calibration information is received. In some non-limiting embodiments, the user may enter calibration information into the display device 107, and the transceiver 101 may receive the calibration information from the display device 107. However, this is not required, and, in some alternative embodiments, the transceiver 101 may receive the calibration information in other ways (e.g., the user may enter the calibration information directly into the transceiver 101). In some non-limiting embodiments, the calibration information may be an analyte measurement using a blood sample (e.g., a finger stick measurement) such as, for example and without limitation, a self-monitoring blood glucose (SMBG) measurement. In some embodiments, the transceiver 101 may calibrate the sensing devices 100 of the sensing system 105 using the received calibration information. In some embodiments, the process 1600 may proceed from step 1626 to step 1624 in which both sensing devices 100 of the sensing system 105 are considered trustworthy.

In some embodiments, the calibration step 1626 may include detecting degradation for each of the sensing devices 100 and adjusting the weightings used to calculate combined analyte concentrations using the detected degradation. In some embodiments, the weightings may be applied to the individual analyte concentrations calculated using measurement information from the sensing devices 100. For example, in some non-limiting embodiments, in step 1626, the transceiver 101 may adjust the weightings so that the individual analyte concentration of a sensing device 100 whose performance has degraded more than the performance of the other sensing device 100 is given less weight than the individual analyte concentration of the other sensing device 100. In some non-limiting embodiments, weightings may be DPARD weightings.

Because, in some non-limiting embodiments, a calibration is performed only when the individual analyte concentrations from the sensing devices 100 are not in agreement and/or when the data patterns from the sensing devices 100 are not trustworthy, the process 1600 may reduce the frequency of calibration relative to a sensing system having only one sensing device. That is, in some non-limiting embodiments, the ability to compare individual analyte concentrations from multiple sensing devices 100 of a sensing system 105 may provide the advantage of reducing the frequency at which calibrations are required. Because a calibration may require a user to take a finger stick measurement, which can be painful, the user may find an analyte monitoring system that requires fewer calibrations desirable.

In some non-limiting embodiments, the transceiver 101 may perform periodically a measurement and read command conveyance process (e.g., process 1400 of FIG. 14 or process 1500 of FIG. 15) to cause the sensing devices 100 of the sensing system 105 to perform measurements sequences and to convey measurement data to the transceiver 101. In some non-limiting embodiments, the transceiver 101 may allow an interval of time to pass between each measurement and read command conveyance process. In some non-limiting embodiments, the interval of time may be, for example and without limitation, 30 seconds, 1 minute, 2 minutes, 5 minutes, 10 minutes, 15 minutes, 30 minutes, and 1 hour. In some non-limiting embodiments, the interval of time may be within a range from 15 seconds to 1 hour, and this range should be understood as describing and disclosing all range values (including all decimal or fractional values) and sub-ranges within this range. In some non-limiting embodiments, the time interval may vary (e.g., based on the remaining battery power of the transceiver 101). In some non-limiting embodiments, steps 1604, 1610, 1616, 1620, and 1624 may be configured to allow the interval of time to pass since the previous measurement and read command conveyance process before initiating a subsequent measurement and read command conveyance process.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A sensing system comprising:
   an interface device;
   a shared communication device connected to the interface device;
   a first analyte sensing device connected to the shared communication device and configured to perform a first measurement sequence in response to receiving an unaddressed measurement command via the interface device and the shared communication device; and
   a second analyte sensing device connected to the shared communication device and configured to perform a second measurement sequence in response to receiving the unaddressed measurement command via the interface device and the shared communication device, wherein the first and second measurement sequences are different.

2. The sensing system of claim 1, further comprising a third analyte sensing device connected to the shared communication device and configured to perform a third measurement sequence in response to receiving the unaddressed measurement command via the interface device and the shared communication device, wherein the third measurement sequence is different than the first and second measurement sequences.

3. The sensing system of claim 1, wherein the first analyte sensing device is configured to perform the first measurement sequence at the same time that the second analyte sensing device performs the second measurement sequence.

4. The sensing system of claim 3, wherein the first measurement sequence is configured to turn a light source of the first sensing device on at times different from times at which the second measurement sequence turns a light source of the second sensing device on.

5. The sensing system of claim 1, wherein the first analyte sensing device is configured to:
   receive an addressed measurement command via the interface device and the shared communication device;
   determine whether the addressed measurement command is addressed to the first analyte sensing device;
   if the addressed measurement command is determined to be addressed to the first analyte sensing device, perform a measurement sequence; and
   if the addressed measurement command is determined to be not addressed to the first analyte sensing device, not perform a measurement sequence in response to the addressed measurement command.

6. The sensing system of claim 5, wherein the measurement sequence performed by the first analyte sensing device in response to the addressed measurement command is the first measurement sequence.

7. The sensing system of claim 1, wherein the first analyte sensing device is configured to:
   receive an addressed read measurement data command via the interface device and the shared communication device;
   determine whether the addressed read measurement data command is addressed to the first analyte sensing device;
   if the addressed read measurement data command is determined to be addressed to the first analyte sensing device, convey measurement data via the shared communication device and interface device; and
   if the addressed read measurement data command is determined to be not addressed to the first analyte sensing device, not convey measurement data in response to the addressed read measurement data command.

8. The sensing system of claim 1, wherein the first analyte sensing device comprises a light source, and the first measurement sequence comprises measuring one or more characteristics of the light source.

9. The sensing system of claim 1, wherein the interface device is an inductive element.

10. The sensing system of claim 1, further comprising a sensor housing, wherein the interface device, shared communication device, and first and second analyte sensing devices are contained within the sensor housing.

11. The sensing system of claim 1, wherein the shared communication device comprises shared wires.

12. A method comprising:
   receiving an unaddressed measurement command at first and second analyte sensing devices of a sensing system via an interface device and shared communication device of the sensing system;
   using the first analyte sensing device to perform a first measurement sequence in response to receiving the unaddressed measurement command;
   using the second analyte sensing device to perform a second measurement sequence in response to receiving the unaddressed measurement command, wherein the first and second measurement sequences are different.

13. The method of claim 12, further comprising:
   receiving the unaddressed measurement command at a third analyte sensing devices of the sensing system via the interface device and the shared communication device of the sensing system; and
   using the third analyte sensing device to perform a third measurement sequence in response to receiving the unaddressed measurement command, wherein the third measurement sequence is different than the first and second measurement sequences.

14. The method of claim 12, wherein the first analyte sensing device is configured to perform the first measurement sequence at the same time that the second analyte sensing device performs the second measurement sequence.

15. The method of claim 14, wherein using the first analyte sensing device to perform the first measurement sequence comprises turning a light source of the first analyte sensing device on at times different from times at which the second measurement sequence turns a light source of the second sensing device on.

16. The method of claim 12, further comprising:
receiving an addressed measurement command at the first and second analyte sensing devices of the sensing system via the interface device and the shared communication device of the sensing system;
using the first analyte sensing device to determine whether the addressed measurement command is addressed to the first analyte sensing device;
using the first analyte sensing device to perform a measurement sequence in response to the addressed measurement command if the first analyte sensing device determines that the addressed measurement command is addressed to the first analyte sensing device, wherein the first analyte sensing device does not perform a measurement sequence in response to the addressed measurement command if the first analyte sensing device determines that the addressed measurement command is not addressed to the first analyte sensing device;
using the second analyte sensing device to determine whether the addressed measurement command is addressed to the second analyte sensing device; and
using the second analyte sensing device to perform a measurement sequence in response to the addressed measurement command if the second analyte sensing device determines that the addressed measurement command is addressed to the second analyte sensing device, wherein the second analyte sensing device does not perform a measurement sequence in response to the addressed measurement command if the second analyte sensing device determines that the addressed measurement command is not addressed to the second analyte sensing device.

17. The method of claim 16, wherein the measurement sequence performed by the first analyte sensing device in response to the addressed measurement command is the first measurement sequence, and the measurement sequence performed by the second analyte sensing device in response to the addressed measurement command is the second measurement sequence.

18. The method of claim 12, further comprising:
receiving an addressed read measurement data command at the first and second analyte sensing devices of the sensing system via the interface device and the shared communication device of the sensing system;
using the first analyte sensing device to determine whether the addressed read measurement data command is addressed to the first analyte sensing device;
using the first analyte sensing device to convey measurement data if the first analyte sensing device determines that the addressed read measurement data command is addressed to the first analyte sensing device, wherein the first analyte sensing device does not convey measurement data if the first analyte sensing device determines that the addressed read measurement data command is not addressed to the first analyte sensing device;
using the second analyte sensing device to determine whether the addressed read measurement data command is addressed to the second analyte sensing device; and
using the second analyte sensing device to convey measurement data if the second analyte sensing device determines that the addressed read measurement data command is addressed to the second analyte sensing device, wherein the second analyte sensing device does not convey measurement data if the second analyte sensing device determines that the addressed read measurement data command is not addressed to the second analyte sensing device.

19. The method of claim 12, wherein using the first analyte sensing device to perform the first measurement sequence comprises measuring one or more characteristics of a light source of the first analyte sensing device.

20. The method of claim 12, wherein the interface device is an inductive element.

21. A sensing system comprising:
an interface device;
a shared communication device connected to the interface device;
a first analyte sensing device connected to the shared communication device and configured to:
  receive an unaddressed measurement command via the interface device and the shared communication device,
  perform a measurement sequence in response to receiving the unaddressed measurement command,
  receive an addressed read measurement data command via the interface device and the shared communication device,
  determine whether the addressed read measurement data command is addressed to the first analyte sensing device,
  if the addressed read measurement data command is determined to be addressed to the first analyte sensing device, convey measurement data via the shared communication device and interface device; and
  if the addressed read measurement data command is determined to be not addressed to the first analyte sensing device, not convey measurement data in response to the addressed read measurement data command; and
a second analyte sensing device connected to the shared communication device and configured to:
  receive the unaddressed measurement command via the interface device and the shared communication device,
  perform a measurement sequence in response to receiving the unaddressed measurement command,
  receive the addressed read measurement data command via the interface device and the shared communication device,
  determine whether the addressed read measurement data command is addressed to the second analyte sensing device,
  if the addressed read measurement data command is determined to be addressed to the second analyte sensing device, convey measurement data via the shared communication device and interface device; and
  if the addressed read measurement data command is determined to be not addressed to the second analyte sensing device, not convey measurement data in response to the addressed read measurement data command.

22. The sensing system of claim 21, further comprising a third analyte sensing device connected to the shared communication device and configured to:

receive the unaddressed measurement command via the interface device and the shared communication device, perform a measurement sequence in response to receiving the unaddressed measurement command, receive the addressed read measurement data command via the interface device and the shared communication device, determine whether the addressed read measurement data command is addressed to the third analyte sensing device, if the addressed read measurement data command is determined to be addressed to the third analyte sensing device, convey measurement data via the shared communication device and interface device; and if the addressed read measurement data command is determined to be not addressed to the third analyte sensing device, not convey measurement data in response to the addressed read measurement data command.

23. The sensing system of claim 21, wherein the shared communication device comprises shared wires.

24. A method comprising:

receiving an unaddressed measurement command at first and second analyte sensing devices of a sensing system via an interface device and shared communication device of the sensing system;

using the first analyte sensing device to perform a measurement sequence in response to receiving the unaddressed measurement command;

using the second analyte sensing device to perform a measurement sequence in response to receiving the unaddressed measurement command;

receiving an addressed read measurement data command at the first and second analyte sensing devices of the sensing system via the interface device and the shared communication device of the sensing system;

using the first analyte sensing device to determine whether the addressed read measurement data command is addressed to the first analyte sensing device;

using the first analyte sensing device to convey measurement data if the first analyte sensing device determines that the addressed read measurement data command is addressed to the first analyte sensing device, wherein the first analyte sensing device does not convey measurement data if the first analyte sensing device determines that the addressed read measurement data command is not addressed to the first analyte sensing device;

using the second analyte sensing device to determine whether the addressed read measurement data command is addressed to the second analyte sensing device; and using the second analyte sensing device to convey measurement data if the second analyte sensing device determines that the addressed read measurement data command is addressed to the second analyte sensing device, wherein the second analyte sensing device does not convey measurement data if the second analyte sensing device determines that the addressed read measurement data command is not addressed to the second analyte sensing device.

25. The method of claim 24, further comprising:

receiving the unaddressed measurement command at a third analyte sensing devices of the sensing system via the interface device and the shared communication device of the sensing system;

using the third analyte sensing device to perform a measurement sequence in response to receiving the unaddressed measurement command;

receiving the addressed read measurement data command at the third analyte sensing device of the sensing system via the interface device and the shared communication device of the sensing system;

using the third analyte sensing device to determine whether the addressed read measurement data command is addressed to the third analyte sensing device;

using the third analyte sensing device to convey measurement data if the third analyte sensing device determines that the addressed read measurement data command is addressed to the third analyte sensing device, wherein the third analyte sensing device does not convey measurement data if the third analyte sensing device determines that the addressed read measurement data command is not addressed to the third analyte sensing device.

* * * * *